United States Patent [19]

Chaco

[11] Patent Number: 5,291,399
[45] Date of Patent: Mar. 1, 1994

[54] METHOD AND APPARATUS FOR ACCESSING A PORTABLE PERSONAL DATABASE AS FOR A HOSPITAL ENVIRONMENT

[75] Inventor: John Chaco, Seymour, Conn.

[73] Assignee: Executone Information Systems, Inc., Darien, Conn.

[21] Appl. No.: 559,196

[22] Filed: Jul. 27, 1990

[51] Int. Cl.⁵ ............................................ G06F 15/00
[52] U.S. Cl. ............................... 364/413.02; 235/375; 235/377; 235/378; 235/380; 364/413.03
[58] Field of Search ...................... 364/413.01, 413.02, 364/413.03; 235/375, 380, 376, 377, 382, 378

[56] References Cited

U.S. PATENT DOCUMENTS

| | | |
|---|---|---|
| 3,439,320 | 4/1969 | Ward . |
| 3,478,344 | 11/1969 | Schwetzgebel et al. . |
| 3,604,900 | 9/1971 | Kalt . |
| 3,696,384 | 10/1972 | Lester ................................. 367/199 |
| 3,739,329 | 6/1973 | Lester ..................................... 367/6 |
| 3,925,762 | 12/1975 | Heitlinger et al. ............. 340/870.09 |
| 3,971,916 | 7/1976 | Moreno . |
| 4,001,550 | 1/1977 | Schatz . |
| 4,052,567 | 10/1977 | MacKay .............................. 370/85.9 |
| 4,126,768 | 11/1978 | Grenzow . |
| 4,216,462 | 8/1980 | McGarth et al. ............. 364/413.03 |
| 4,225,953 | 9/1986 | Simon et al. ........................ 367/117 |
| 4,532,419 | 7/1985 | Takeda . |
| 4,536,646 | 8/1985 | Adams et al. ....................... 235/377 |
| 4,553,267 | 11/1985 | Crimmins .......................... 359/145 |
| 4,649,385 | 3/1987 | Aires et al. ............................ 379/57 |
| 4,650,981 | 3/1987 | Foletta . |
| 4,680,790 | 7/1987 | Packard et al. ..................... 379/432 |
| 4,692,604 | 9/1987 | Billings . |
| 4,748,668 | 5/1988 | Shamir et al. . |
| 4,757,553 | 7/1988 | Crimmins .......................... 359/114 |
| 4,780,601 | 10/1988 | Vermesse . |
| 4,795,890 | 1/1989 | Goldman . |
| 4,795,897 | 1/1989 | Chalendard . |
| 4,798,322 | 1/1989 | Bernstein et al. . |
| 4,810,864 | 3/1989 | Takahashi . |
| 4,813,879 | 3/1989 | Thenaisie et al. . |
| 4,825,052 | 4/1989 | Chemin et al. . |
| 4,835,372 | 5/1989 | Gombrich et al. ................. 235/375 |
| 4,841,133 | 6/1989 | Gercekci et al. . |
| 4,849,615 | 7/1989 | Mollet . |
| 4,853,692 | 8/1989 | Wolk et al. . |
| 4,864,110 | 9/1989 | Guillou . |
| 4,874,935 | 10/1989 | Younger ............................. 235/492 |
| 4,882,473 | 11/1989 | Bergeron et al. .................. 235/380 |
| 4,893,001 | 1/1990 | Ohkubo et al. . |
| 4,893,330 | 1/1990 | Franco . |
| 4,899,373 | 2/1990 | Lee et al. . |
| 4,955,000 | 9/1990 | Nastrom ............................. 367/117 |
| 4,977,619 | 12/1990 | Crimmins .......................... 359/172 |
| 5,038,800 | 8/1991 | Oba .................................... 128/904 |
| 5,077,666 | 12/1991 | Brimm et al. .................. 364/413.02 |

FOREIGN PATENT DOCUMENTS

| | | |
|---|---|---|
| 2190525A | 11/1987 | United Kingdom . |
| 2193359A | 2/1988 | United Kingdom . |
| 2230365A | 10/1990 | United Kingdom . |

OTHER PUBLICATIONS

Matsunobu & Wong, "Kapiolani Women's and Children's Medical Center," *Computers in Health Care*, Jun. 1986, pp. 20-26.

(List continued on next page.)

Primary Examiner—Roy N. Envall, Jr.
Assistant Examiner—Stephen R. Tkacs
Attorney, Agent, or Firm—Dilworth & Barrese

[57] ABSTRACT

A distributed data processing network includes multiple memory card databases at terminal nodes of the network. The network is programmed to automatically perform routine communications operations such as conveying identification information between the terminal nodes and interior nodes. The network is implemented in a hospital environment and the databases include information on patients and hospital personnel. Using the automatic communications facilities of the network patient information from the database is displayed at a nurse station when the patient initiates a nurse-call or automatically when medication, also recorded on the card, is due. In addition, the system may be used to locate hospital personnel and equipment, to audit the use of controlled substances and to automatically assemble emergency response teams.

18 Claims, 24 Drawing Sheets

OTHER PUBLICATIONS

Ooi, Lim & Lau, "Low Cost RF Identification and Locating System," *IEEE Transactions on Consumer Electronics*, vol. 35, No. 4, Nov. 1989, pp. 831–839.

Davies & Wakerly, "Synchronization and Matching in Redundant Systems" *IEEE Transactions on Computers*, vol. C-27, No. 6, Jun. 1978, pp 531–539.

Infra-Com ®.

R. C. Livermore, "Health Service Applications in England and Wales," International Conference and Workshop on Smart card Applications and Technologies, 1988, pp. 5–eoa.

Brown, Vallbona & Kitasanono, "A New Patient Record System Using the Laser-Card" *Optical Information Systems*, vol. 8, No. 4, Jul.–Aug., 1988, pp. 156–161.

D. Artusi, "The Technology of Smart Cards and Their Applications," Electro/86 and Mini/Micro Northeast Conference, 1986, pp. 1–8.

Futura & Futura II, Specifications Notice.

M. Siedband, "Data card system for filmless radiography", *Medical Imaging*, vol. 727, part 2, pp. 831–833, 1987.

R. G. Stevens, "Experiments with Computer Card Medication Records in Britain", International Conference and Workshop on Smart card Applications and Technologies, pp. 12–eoa; 1988.

G. B. Latamore, "Smart Cards Get Smarter," *High Technology Business*, pp. 35–37, Sep. 1987.

B. Millar, "A credit card away from better healthcare," The Health Service Journal, vol. 99, No. 5141, Mar. 9, 1989, p. 289.

G. Moore, "The hospital connection" *Computer Systems Europe*, pp. 73–76, May 1989.

T. Kuroiwa, "The application of the I.C. card in the area of medical health", *Proceedings of the Ninth Annual Conference of the IEEE Engineering in Medicine and Biology Society*, vol. 4, pp. 2124–2125, 1987.

M. Oikawa, "Marketing activities in Finland," vol. 1, No. 2, pp. 102–103, 1989.

M. U. Shaffer, J. C. Rios, "Semi-automated heart station", Proceeding of the 26th Annual Conference on Engineering in Medicine and Biology, p. 40 1973.

J. Green, "Niche market growth for cards," Communications International, vol. 15, No. 8, p. 16, Aug. 1988.

NURSE CALL STATION MAIN LOOP

CALL NURSE STATION

STORE DATA ON CARD

PROCESS LIGHT PEN DATA

Fig. 13  BADGE TRANSCEIVER PROCESS

STATIONARY TRANSCEIVER PROCESS

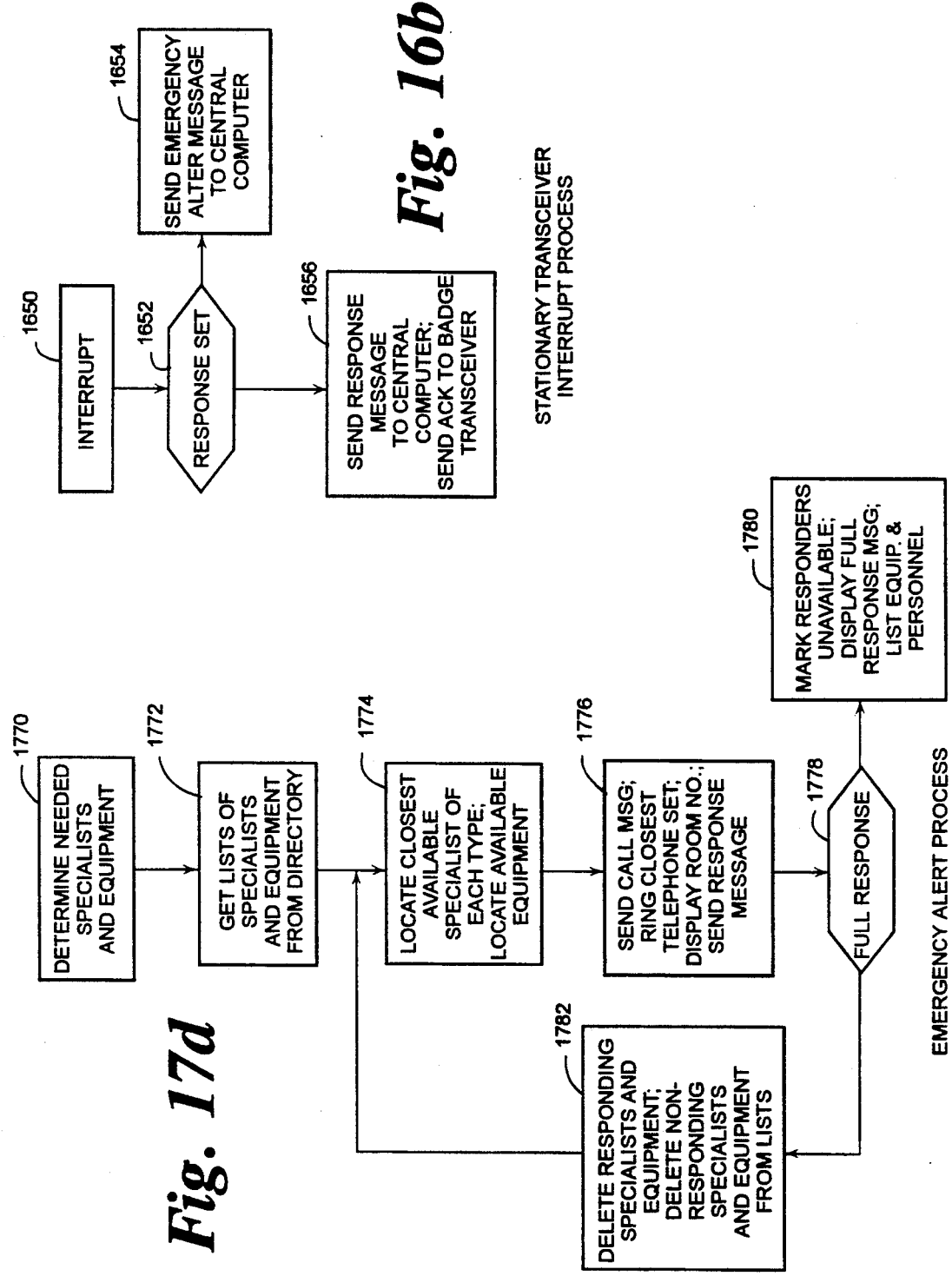

DRUG MONITOR SYSTEM - DRUG LOCKER

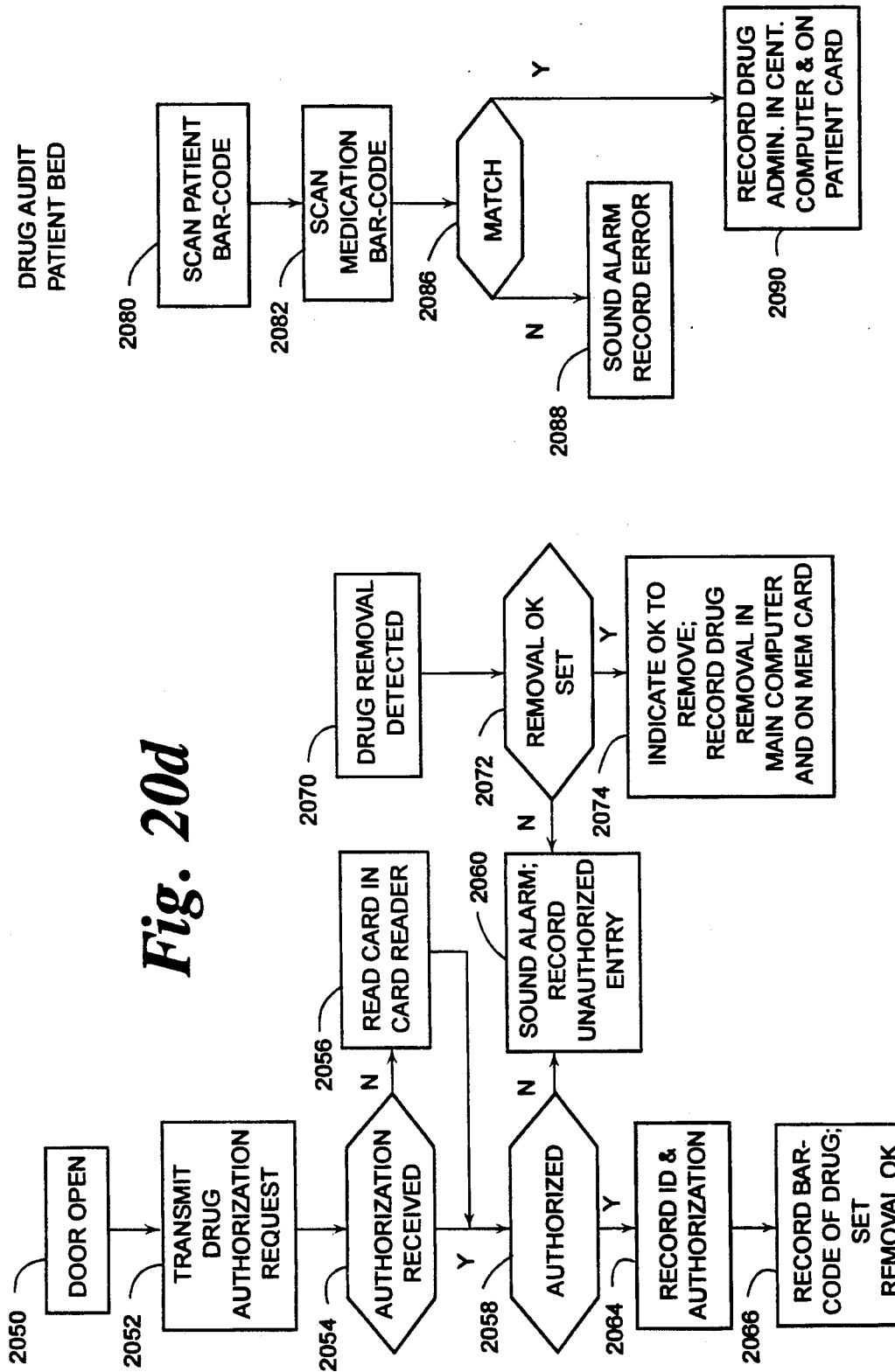

METHOD AND APPARATUS FOR ACCESSING A PORTABLE PERSONAL DATABASE AS FOR A HOSPITAL ENVIRONMENT

FIELD OF THE INVENTION

The present invention is directed to a portable personal database and to apparatus for accessing the database which may be used by patients and caregivers in a hospital environment and in other analogous environments. In particular, the invention concerns such a database implemented in a data storage medium having the portability of a credit card.

BACKGROUND

As medical technology has developed to provide treatments for a greater number of medical conditions, and as hospitals have become automated to cope with chronic personnel shortages, the volume of information that is maintained for each patient has grown rapidly. As a result of this increase in information, it is often difficult for caregivers such as physicians and nurses to quickly find critical data about a patient.

To more fully understand the problem, consider the types of data which may be maintained for an individual patient. The hospital may want to know the name, address and insurance carrier for the patient as well as any special dietary, environmental or physical space requirements. The attending physician may want to know the patient's condition, medical history and recent vital sign data. If the patient has had any diagnostic tests such as X-rays or ultrasound images made at this hospital or at any other hospital, the attending physician may want to compare these test results with the results of newer tests to see how the patient's condition has progressed. In addition, if any medication has been prescribed, the physician may want to know the identity of the medication, when the last dose was taken and how the patient has complied with the dosage schedule.

The nursing staff covering the patient's room may want to have some indication of the patient's condition at the nurse station when the patient presses the nurse call station. For example, if the patient has been admitted for a heart condition, it would be helpful if any recent vital signs that may indicate the onset of a heart attack could be displayed at the nurse's station when patient presses the call button.

This type of information may be especially helpful when, due to a shortage of nurses or to an emergency situation, routine calls must be delayed. This information may also be helpful to a temporary nurse who is not familiar with the patients or with the hospital procedure.

Patient billing presents another data-keeping problem for hospitals. Charges for the physician, diagnostic laboratory and pharmacy may be separate from the hospital charges. In addition, many hospitals are allowing patients to charge non-essential items such as magazines and books to their hospital accounts. Currently, due to the time required to process these items through the hospital billing system and the insurance carrier, the charges that must be paid by the patient may not be known until several months after the hospital stay. Furthermore, some insurance carriers, such as Medicare, pay the physician based on the actual time spent with the patient. Using the present data gathering methods, billing data of this type may be difficult to obtain and to verify.

Recently, memory cards and smart cards have been used to hold a patients billing information and medical records. Three different types of cards, each about the size and thickness of an ordinary credit card, have been used for these purposes. One type of card has a non-volatile memory such as a magnetic stripe or a medium on which information may be recorded using a laser. These cards may hold a relatively large amount of information but this information can only be read by a relatively large and complex card reader. Another type of card includes a non-volatile memory such as an electrically alterable read only memory (EAROM) with external contacts on the surface of the card. Data stored in a memory of this type may be read using circuitry that is relatively inexpensive and compact. The third type of card combines a microprocessor with the non-volatile memory. In this configuration, the card may include programming to implement a security system which is designed to prevent unauthorized access to data on the card.

An exemplary system in which hospital billing information is kept on a memory card is described in an paper by A. Matsunobu et al. entitled "Kapiolanai Women's And Children's Medical Center" Computing Healthcare Vol 7, No. 6 PP 20-26, 1986. A system for keeping patient records on a laser card system is described in a paper by J.H.U. Brown et al. entitled "A New Patient Record System Using The Laser Card" Optical Information Systems, Vol 8, No. 4, PP 156-161 July-August 1988. Two systems which use a memory card to hold patient records are described in a paper by R.C. Livermore entitled, "Health Service Applications In England And Wales" Smart Card 88, PP 5-10, June 1988.

All of these systems merely record the information on the card so that it may be read by a caregiver at a later time. These systems fill a need by allowing the caregiver to obtain the medical records directly from the patient rather than having to request the data from the various hospitals, physicians and pharmacists which have served the patient. None of these systems provide for any automatic interaction with information stored on the card.

Another problem faced by care givers and by hospital administrators is determining the location of key personnel and equipment. In an emergency it may be of critical importance to be able to quickly locate the attending physician and to communicate the nature of-the emergency situation. Moreover, when special equipment is required to treat an emergency condition, it is desirable that this equipment be quickly located with a determination as to its availability.

Current systems for locating personnel within a hospital rely on audio paging systems, sign-in and sign-out sheets and broadcast paging systems. In a given situation, the audio paging system would be tried first. This system may not be effective if the person to be located is in an area where the paging system is not functioning properly or has been turned down, or if the person has left the hospital. After an unsuccessful audio page, the sign-in and sign-out sheets may be checked. If, however, the person to be located forgot to use the sign-out sheet, critical time may be lost in a second attempt to use the audio paging system. In addition, a search of the sign-in and sign-out sheets may require more time than is available in an emergency situation.

When the person to be located is outside of the hospital, broadcast paging systems are often the best way to convey an important message. These systems require the individual trying to locate the person to call a paging service, leave a message, wait for the paging service to send the message to the individual's pocket pager and then wait for the person being paged to call the paging service, receive the message and respond. This system is too time consuming and unwieldy for use inside the hospital environment.

Physicians who have a private practice and who are associated with a hospital may have difficulty receiving emergency calls while they are in the hospital but not in their hospital office. Calls of this type may be handled either through the audio paging system of the hospital or through a broadcast paging system. Neither of these solutions is particularly desirable, since, the physician may not hear or understand the message sent through the audio paging system and may not wish to be interrupted by a pocket beeper while attending to a patient in the hospital.

Another problem with audio paging systems used in a hospital environment is noise pollution. These systems are often louder than necessary and may add an element of stress to an environment where stress is desirably kept to a minimum.

In addition to locating caregivers, it may also be desirable to quickly locate patients who are not in their rooms. This is particularly true for patients that have recently been moved, say from an intensive care unit to a room, or for patients who tend to wander or who have memory problems. Patients such as these may not realize they are being paged through an audio paging system or, if they do, may be unable to respond. In these instances, hospital personnel must be available to search for the patients or the patients must be restrained to prevent them from wandering.

Exemplary existing locator systems use either radio frequency signals or infra-red signals to communicate the position of a mobile individual or object to a network of receivers. One such system, the Infra-Com ™ Locating And Signaling System available from United Identification Systems Corp. is designed for use in a hospital environment. Using this system, a network of infra-red transceivers located throughout a hospital can both transmit data to and receive data from a battery-operated badge worn by hospital personnel or attached to the equipment to be located. This badge transmits a programmed identification signal to the network allowing the position of the badge to be indicated on a floor plan of the hospital.

Another exemplary system, the TELOC PLS Personnel Locator System available from TELOC INC., also uses two-way infra-red signalling to communicate the position of a battery powered badge in a distributed sensor network. In addition, the TELOC system may be coupled to a private branch exchange (PBX) to allow telephone calls for an individual to be routed to the telephone that is closest to the badge or to direct an intercom message to that telephone, thus providing an alternative to an audio paging system.

Each of these systems is limited in the data that may be conveyed between the stationary transceiver network and the transceiver on the badge. In the described systems, only identification information and an indication that switches on the badge have been activated may be transmitted from the badge.

Furthermore, if the transceiver on the badge fails or is damaged, a blank badge must be programmed to take its place. This programming operation may be time consuming, leaving the individual or the piece of equipment invisible to the locating system for that period of time.

Yet another problem faced by hospitals is in preventing unauthorized access to restricted areas, such as drug lockers and hospital pharmacies. Currently, these areas require special security measures, such as guard personnel or complex electronic apparatus to verify the identity of an authorized individual. These security measures are an annoyance to those who are subject to them and may increase the response time to an emergency situation when a critical medication is only available in the drug locker.

Although the discussion so far has focused on the hospital environment, other institutions have similar problems. For example, in correctional institutions, it may be necessary to quickly locate guards or trustees to either respond to a disturbance or to ensure that there is sufficient surveillance of the prison grounds. In an emergency, where, for example, a guard is being attacked by an inmate, it may be desirable for the guard to be able to quickly alert a central facility so that reenforcements may be sent. To provide this type of warning, the guards at many correctional facilities rely on walkie-talkies. When the situation develops quickly, however, there may not be time for the guard to use the walkie-talkie and to protect himself against the attacker.

Many industrial security systems augment electronic intruder detectors with hired guards who follow a fixed route through the facility. To ensure that these guards walk the designated route at the appointed times, the guards may be required to carry a clock mechanism into which keys, found at key-stations along the way, may be inserted. These keys are designed to be inserted only in a prescribed order. The clock mechanism records the time at which the keys were inserted to provide a record of when the guard passed the key station. Systems of this type are subject to abuse if, for example, shortcuts exist between successive key stations. Moreover, the clock mechanisms tend to be bulky and may impede the guard in his investigation of an abnormal situation.

A night watchman at an industrial plant may have the same need as a prison guard to signal for help in an emergency situation, and, like a prison guard may not have time to use a walkie-talkie.

Another institution in which data keeping is important but often burdensome is in colleges and universities. In this environment it may be desirable to know what courses a student is taking, whether the student resides in on-campus housing and, if so, to know the student's address. The college administrators may also want to know if a particular student has an outstanding balance on his tuition bill. In addition, the student may want to be able to charge expenses to an account which is sent directly to his parents.

In many colleges and universities, the databases which keep track of this type of information are not integrated. Some information may only be available from a terminal coupled to a central computer while other information may only be recorded in a paper filing system.

SUMMARY OF THE INVENTION

The present invention is embodied in a portable personal database which contains identifying and other information about an individual and an apparatus, removably coupled to the database and configured to convey data from the database to a remote receiver.

According to a first aspect of the invention, the database includes medical information about the individual in addition to the identifying information. The apparatus includes a nurse call station, configured to accept the personal database and to convey the medical information along with the identifying information to a central nurses station when a nurse call operation is initiated.

According to a second aspect of the invention, the database is augmented by machine-readable identifying information attached to the individual, and the apparatus includes means for reading the attached machine-readable identifying information, for verifying it against the identifying information in the personal database and for conveying any mismatch between the machine-readable information and the identifying information in the database to the remote receiver.

According to a third aspect of the invention, the apparatus includes means for conveying, to the remote receiver, the elapsed time that the database is coupled to the apparatus in addition to conveying the identifying information.

According to a fourth aspect of the invention, the apparatus includes a radio transmitter which broadcasts a radio signal to convey the information to the remote receiver.

According to a fifth aspect of the invention, the apparatus includes a receiver and a transmitter which may be physically coupled to the database and a remote transmitter coupled to the remote receiver for transmitting a signal to the receiver to condition the transmitter to send the identifying information to the remote receiver.

According to a sixth aspect of the invention, the apparatus includes switch means for increasing the power applied to the radio transmitter to increase the strength of the signal provided by the radio transmitter to the remote receiver.

According to a seventh aspect of the invention, a plurality of remote receivers and remote transmitters are coupled to a telephone system and the telephone system includes apparatus that determines which of the remote receivers is close to the database and that routes a signal for the individual identified by the database to a telephone set which is physically close to the database.

According to an eighth aspect of the invention, the apparatus is coupled to a telephone set which is coupled to a telephone network and the remote receiver is coupled to another telephone set coupled to the telephone network and the remote receiver includes means for changing information in the database while it is coupled to the telephone network.

BRIEF DESCRIPTION OF THE DRAWINGS

FIGS. 5 through 10 are flow-chart diagrams which illustrate the operation of the nurse call station shown in FIG. 2.

FIGS. 16a and 16b are flow-chart diagrams which illustrate the operation of the transmitter receiver unit shown in FIG. 15.

FIGS. 17c and 17d are flow-chart diagrams which illustrate the use of the system as a personnel and equipment locator and for handling an emergency alert condition.

FIG. 20b is a block diagram of a drug locker monitoring system suitable for use with the drug locker shown in FIG. 20a.

FIGS. 20d and 20e flow-chart diagrams which illustrate the operation of a drug auditing system using the drug locker monitoring system shown in FIG. 20b and the nurse call station shown in FIG. 4.

FIG. 21b is a flow-chart diagram which illustrates the operation of a student-advance electronic funds transfer system which may be implemented on the student information system shown in FIG. 21a.

DETAILED DESCRIPTION

Overview

The present invention has application wherever routine communication may be automated. Many of the features of this invention may be illustrated by a system implemented in a hospital environment. Accordingly, for the sake of brevity, the detailed description of the invention presented below is primarily shown in a hospital environment. It is contemplated, however, that the invention has a much broader range of applications.

All of the exemplary embodiments of the invention described below use a memory card as a personal database. As used herein, a memory card is defined to be an electronic device approximately the same size and shape as an ordinary credit card which includes a nonvolatile programmable memory. In the card used in the embodiments described below, the memory is an electronically erasable read only memory (EEROM) located internal to the card. It is contemplated, however, that other forms of internal memory, such as a ferroelectric RAM or a CMOS memory with an integral battery, may be used. It is also contemplated that the functions described below may be implemented with external memories, such as magnetic stripe or laser card technologies which either augment or replace the internal memory.

Figure 2:
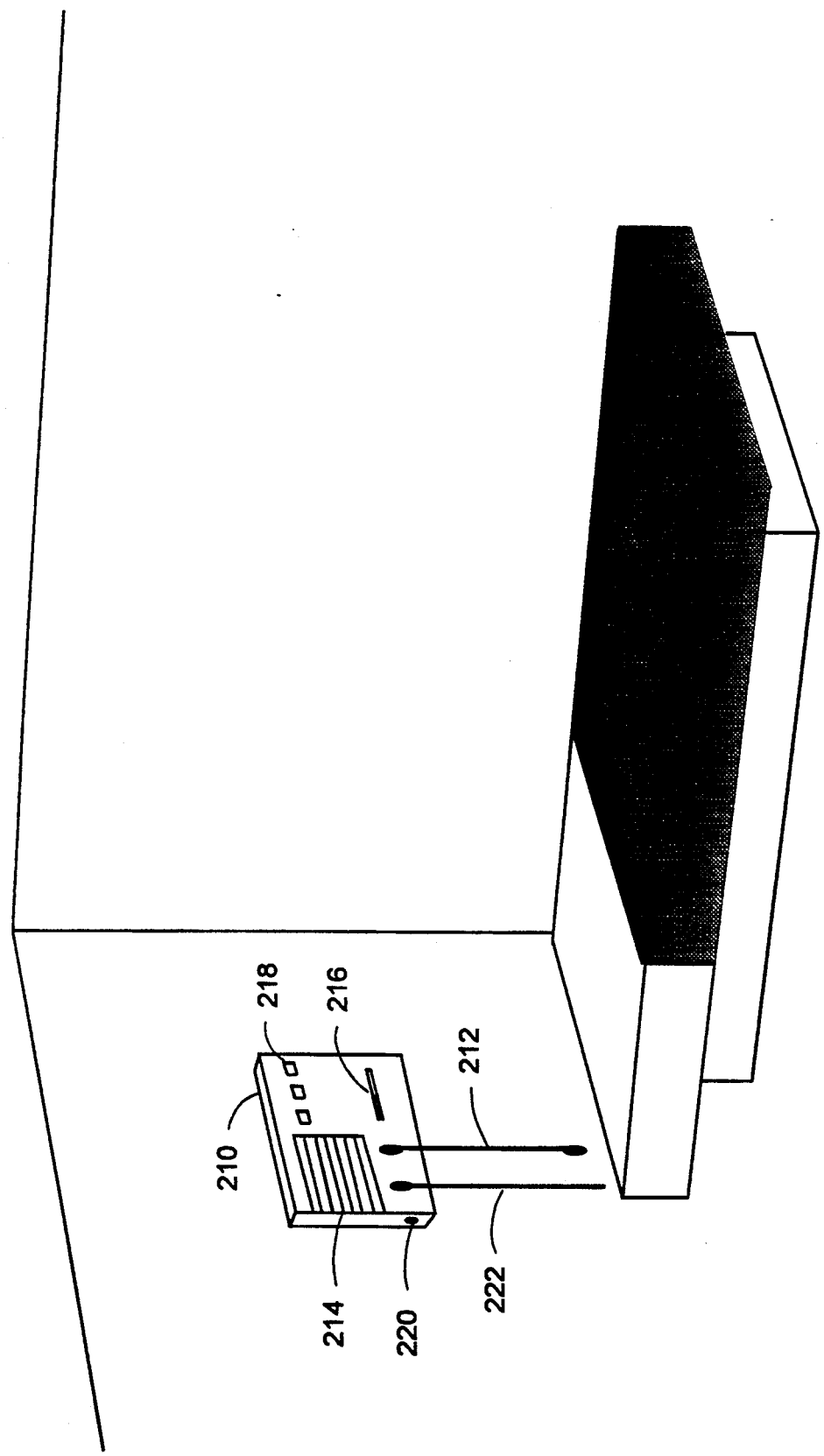
FIG. 2 is a perspective drawing of a portion of a patient room which includes a nurse call station suitable for use in the present invention.

The first embodiment of the invention described below uses the memory card to augment the features that may be provided by a nurse call station in a hospital. FIG. 2 shows a typical hospital bed located in close proximity to a nurse call station 210. A memory card containing, for example, the patient's name and reason for admission as well as an abbreviated medical history is inserted in slot 216 of the call station 210. When the patient squeezes the bulb of the nurse call device 212, the call station 210 transmits selected information stored on the card to the central nurse station where it is displayed on a CRT monitor.

The information stored in the card may include prescription information and, optionally, the most recent few minutes of vital sign data, such as may be provided by an electrocardiogram, for example. This display enables the nurse at the station to quickly determine the importance of a call and to respond accordingly. As described in detail below, the card may be programmed with prescribed medication for the patient. In this instance, a call to the central nurse station may be automatically generated to remind the duty nurse that it is time to administer the medication.

Figure 11B:
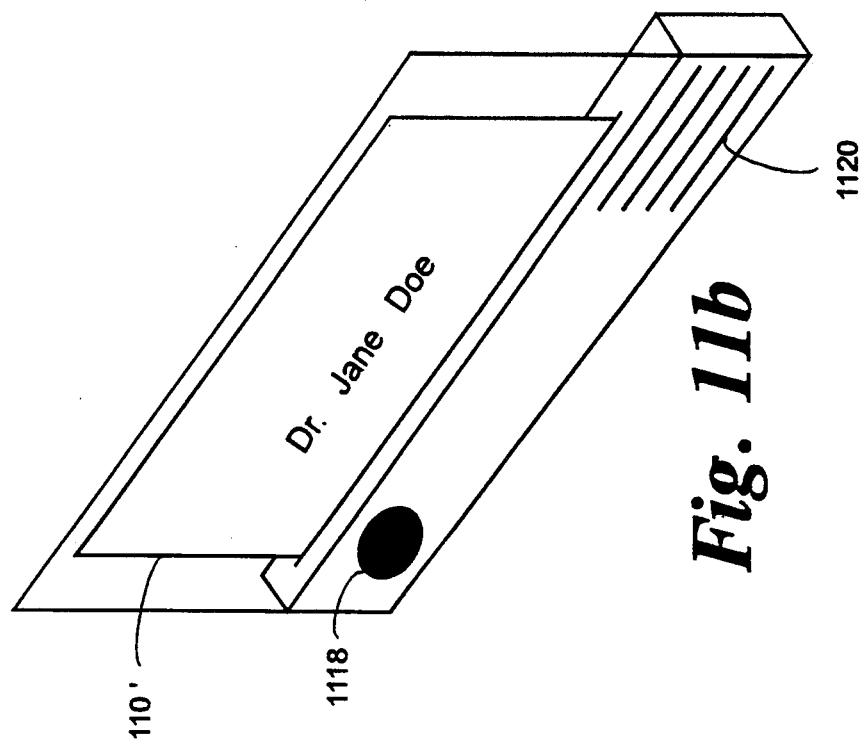
FIGS. 11a and 11b are perspective drawings of a portable transceiver unit suitable for use with the present invention.
Figure 11A:
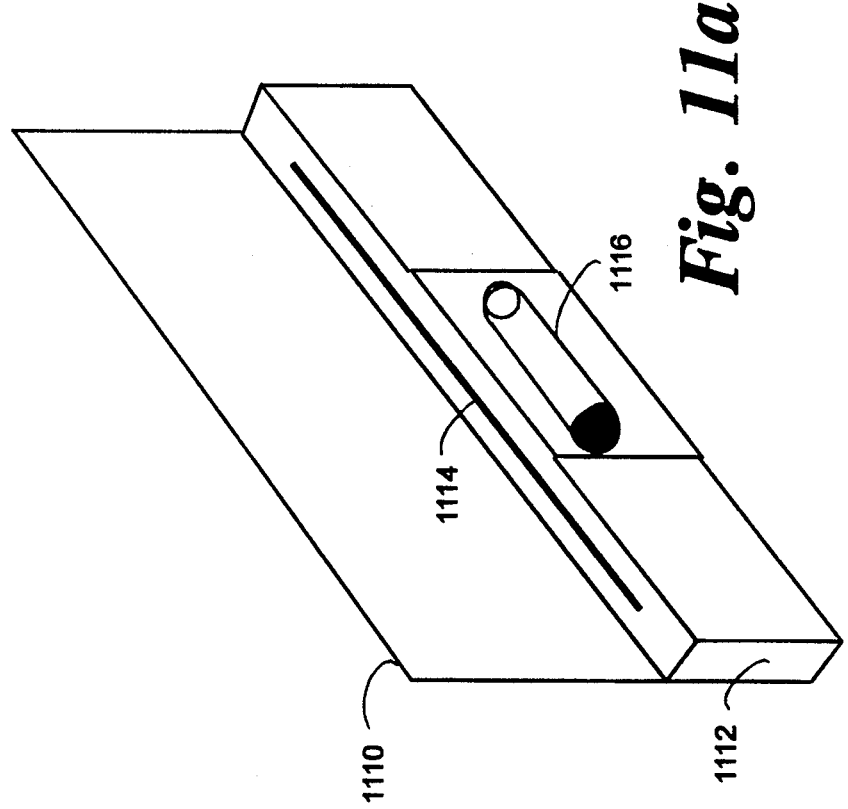

In addition to the nurse station interface to the memory card, a broadcast interface is described with reference to FIGS. 11 through 16. This portable interface has similar data communications capability to the nurse call station interface. In this implementation of the invention, the memory card functions as an identification badge. The card is coupled to a small portable transceiver as shown in FIGS. 11a and 11b. Data on the card may be transmitted to and received from fixed transceivers located, for example, in telephone sets distributed around the hospital. In addition to performing routine communication, such as signing into and out of the hospital, the combination of the memory card and the transmitter can be used to locate key personnel and equipment, to ease the security requirements for accessing controlled substances and to forward calls to a telephone located in close proximity to the person being called.

In another described embodiment, the smart card is used with a secure data communications device to automate billing operations, such as those for Medicare, where the amount the physician may bill is determined, at least in part, by the amount of time spent with the patient. This device, which would remain in the physician's office, records the amount of time that the patient's card is inserted and automatically reports all patient activity to a central database at the end of the day. This embodiment of the invention is described with reference to FIGS. 17 and 18.

An embodiment of the invention which automatically audits the use of controlled substances, such as medication in a drug locker, is described with reference to FIGS. 20a through 20e. This system automatically records the identity of the person removing the drugs and the drugs that are removed. In addition, the system records when the drugs are administered and the identity of the patient to whom they are given.

A final embodiment of the invention is described with reference to FIGS. 21a and 21b. This embodiment concerns uses of a memory card in an academic environment. In one described use of the card, a student may receive an electronic funds transfer, which is recorded on the card, using a special telephone located in his dormitory room. The card may also be used to allow the student to gain read-only access to centrally stored academic data or to gain read-write access to a campus bulletin board.

DETAILED DESCRIPTION OF EXEMPLARY EMBODIMENTS OF THE INVENTION

Figure 1A:
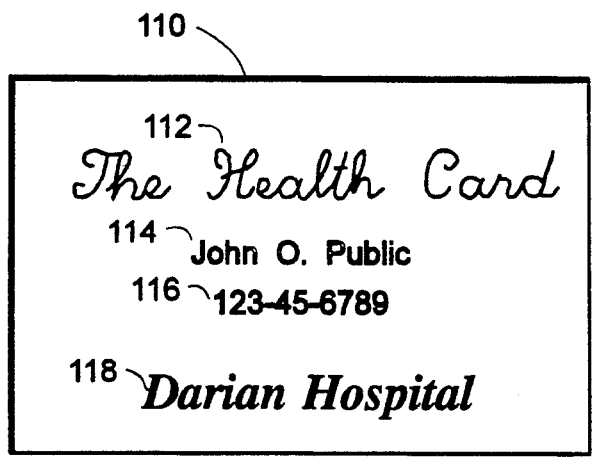
FIGS. 1a and 1b are respective front plan and back plan drawings of a personal database suitable for use in the present invention.
Figure 1B:
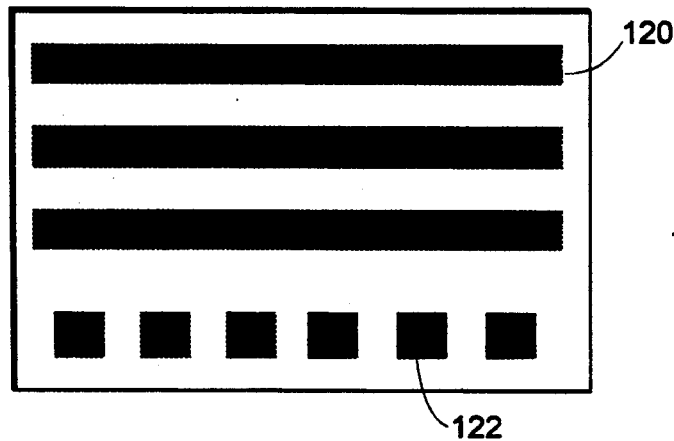

The memory card 110 used with these exemplary embodiments of the invention is illustrated in FIGS. 1a and 1b. As shown in FIG. 1a, the card 110 is approximately the same size and has the same physical characteristics as an ordinary credit card. The front of the card may include a printed logo, 112, which identifies the provider of the card, identifying information such as the patient's name, 114 and ID number 116, as well as a legend, 118, identifying the hospital that issued the card.

The back of the card may include auxiliary, external data storage 120 and electrical contacts 122 for interfacing with the internal circuitry of the card. The auxiliary data storage 120 may include magnetic stripes, as shown in FIG. 1a, or a medium compatible with a laser card device. The electrical contacts 122 may be in the form of ohmic contacts, as shown in FIG. 1b or electromagnetic contacts, such as are disclosed in U.S. Pat. No. 4,798,322 to Bernstein et al. CARD READER/WRITER STATION FOR USE WITH A PERSONAL MEMORY CARD USING DIFFERENTIAL DATA TRANSFER.

An exemplary memory card, which uses ohmic contacts and does not have any auxiliary data storage is the memory card component of the PC3 TM system available from PC3 Inc. This exemplary memory card includes 16,384 (16k) bytes of EEROM. The exact format of the data on the card is unimportant for this description of the invention since it would change with the application. For use in a hospital patient data system, the card should include information such as the patient's name, address and telephone number, her age and blood group, an indication of any chronic condition from which she suffers and any allergies that she may have. In addition it should indicate the name and address of her personal physician, the date of her most recent tetanus shot, and the identity and dosage schedule of any prescribed medicine. For most patients, all of this information may be recorded in 2k bytes of storage in the card, leaving 14k available for other uses.

As shown in FIG. 1b, it is contemplated that the card may also include auxiliary storage such as a laser recording medium. This storage may be used to hold digitally compressed radiographic images or other data that cannot feasibly be stored in the card memory.

Figure 1D:
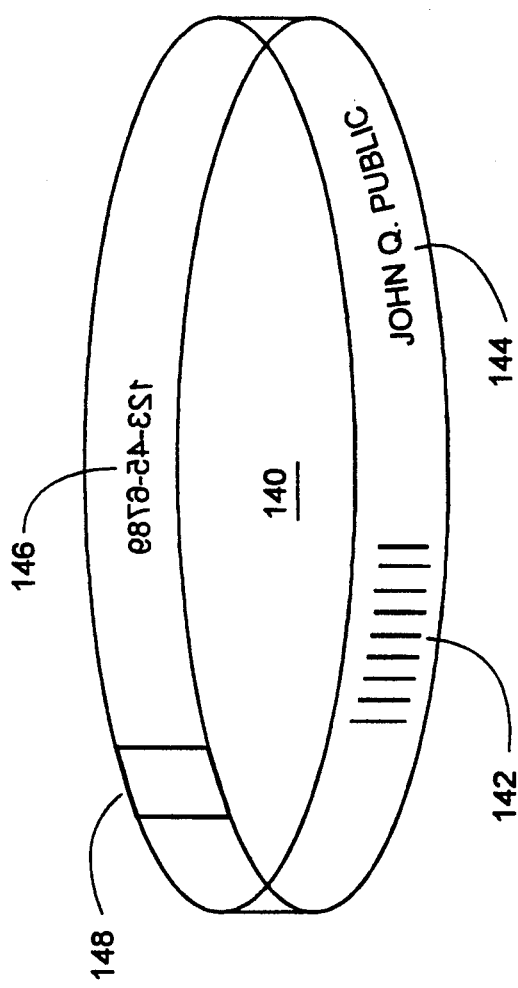
FIG. 1d is a perspective drawing of a patient wrist band.

One useful piece of information is a bar-code ID number which is stored onto the card from a bracelet that is attached to the patient so that it is difficult to remove. An exemplary bracelet of this type is shown in FIG. 1d. The bracelet 140 also includes the patient's name, 144, and ID number 146. The bracelet is configured to be closed, using a clamp 148, around the wrist or ankle of the patient so that it cannot be slipped over the patient's hand or foot, respectively. The use of the bar-code information is described below in reference to FIGS. 9 and 20e.

Figure 1C:
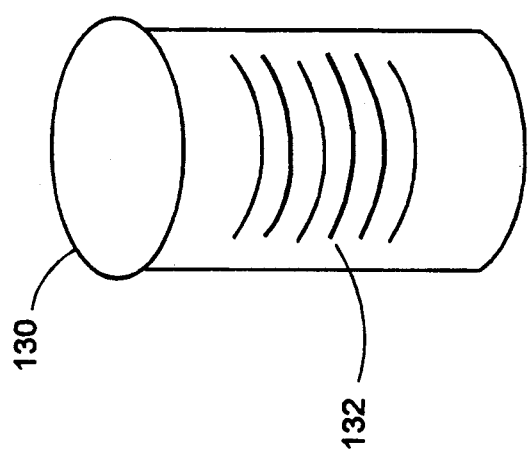
FIG. 1c is a perspective drawing of a patient medicine container.

Another component of the system is a bar-code 132 that is placed on medication containers 130, as shown in FIG. 1c. This bar-code is used, as described below in reference to FIGS. 9 and 20e to identify medicines to the central computer to ensure that the proper medicine is being administered to the patient and to audit the use of controlled substances in the hospital.

An exemplary configuration for the patient's nurse call station is shown in FIG. 2. The exemplary call station 210 includes a slot 216 into which the memory card 110 may be inserted and a squeeze bulb 212, which, when squeezed, alerts the duty nurse at the central nurse station that the person in the bed needs assistance. In addition, the call station may include a speaker 214 through which the duty nurse may both talk to and listen to the patient, push button switches 218, one of which may be used to cancel a call, a light pen 222 for reading the bar-codes such as those on the wrist band and on the medication, one or more external data inputs 220 which may be used to supply vital sign data to the central nurse station.

Figure 3:
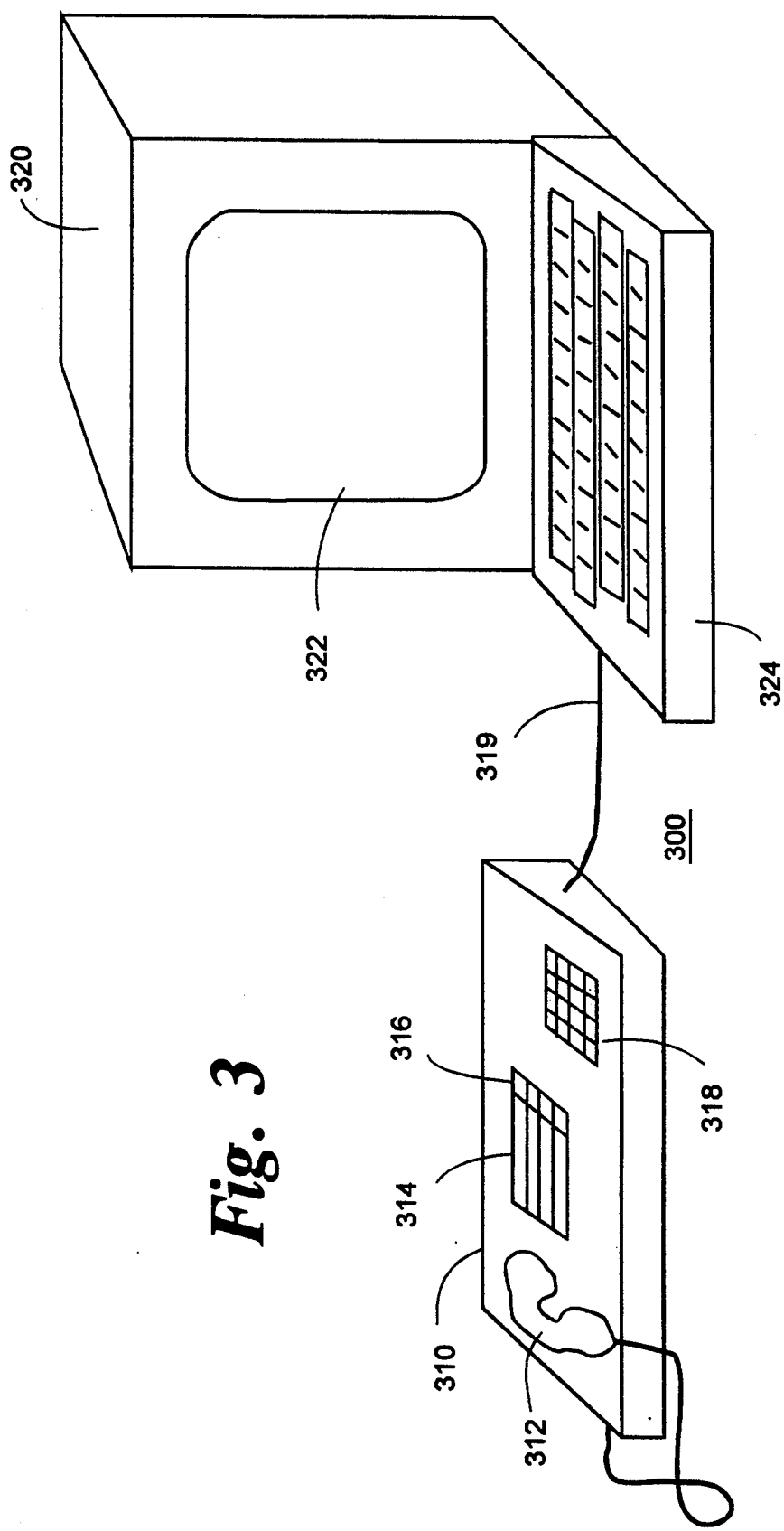
FIG. 3 is a perspective drawing of a central nurse station suitable for use with the present invention.

An exemplary central nurse station 300 is illustrated in FIG. 3. The central components of the nurse station are a telephone console 310 and a microcomputer terminal 320. The telephone console 310 includes a standard telephone handset 312 and keypad 318. In addition, the exemplary console includes a display 314 which indicates the room numbers for patients who have called and an auxiliary display 316 which displays a call priority.

Additional data on the calling patients may be displayed on a video screen 322 of the microcomputer 320. Patient data, such as prescribed medication or menu choices, may be entered into the central computer using the keyboard 324 of the microcomputer terminal 320. As set forth below, this data may also be written onto the patient's memory card.

Figure 4:
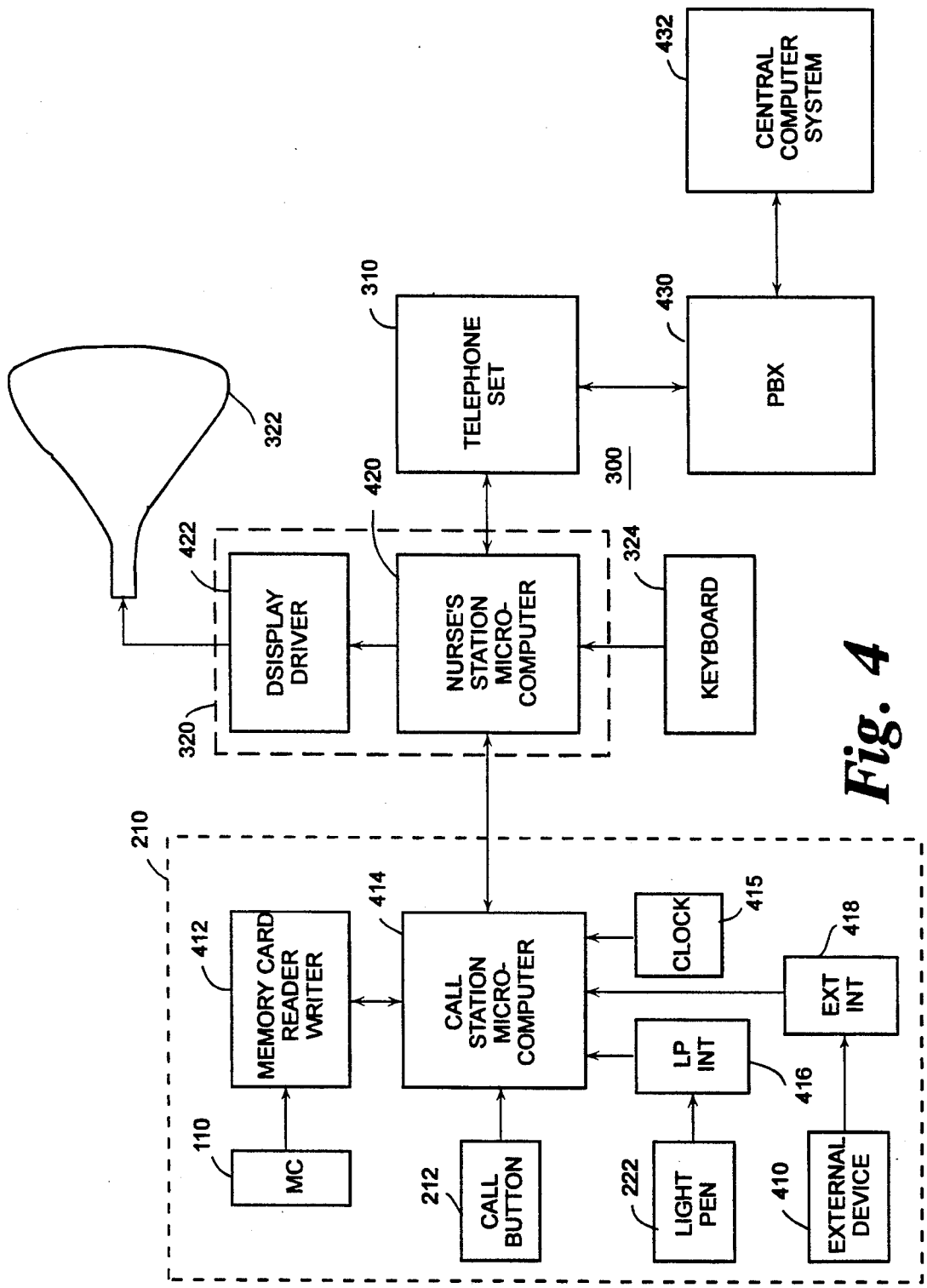
FIG. 4 is a block diagram showing the functional connectivity of the nurse call station and central nurse station shown in FIGS. 2 and 3.

FIG. 4 is a block diagram which illustrates the functional interconnection of the various items illustrated in FIGS. 1a, 1b, 2 and 3. As shown in FIG. 4, the nurse call station 210 includes a memory card reader/writer, 412, into which the memory card 110 may be inserted. The reader/writer 412, which may be, for example, the PC3 ™ memory card reader/writer available from PC3 Inc. is coupled to a call station microcomputer 414 by a two-way data link.

The microcomputer 414 used in the exemplary embodiment of the invention uses an 80C50 microcontroller, manufactured by Intel Corp. A read only memory (ROM) program storage and random access memory (RAM) for temporary data storage. The nurse call button 212 is coupled to a serial data input port of the microcomputer 414. The light pen 222 is coupled to the microcomputer 414 through a light pen interface circuit 416. A light pen interface circuit suitable for use in the nurse call station 210 is the PC E-Z-Reader ™ 300/5G111 model available from PC E-Z-Reader Inc.

One or more external devices, such as an electrocardiogram, blood pressure monitor or respiration monitor may be coupled to the microcomputer 414 through separate external interface circuits 418. The type of external interface circuit used depends on the type of device which is to be monitored. If the device includes standard data interface, such as an RS232 port or an IEEE 488 port, the external interface 418 may be one of the serial interface ports to the microcomputer 414. If, however, the external device 410 can only provide an analog output signal, the external interface circuit 418 may include apparatus such as an analog-to-digital converter (ADC) (not shown) to develop digital samples representing the analog waveform.

In the exemplary embodiment of the invention, digital samples of the data to be monitored are stored in a circular buffer implemented in the memory card 110. The number of bytes in the buffer is fixed at, for example, 1024 and byte address are generated by a modulo 1024 counter. Thus, new data is continually overwriting old data. In this configuration, each circular buffer holds samples representing a fixed time interval. If, for example, the buffer is limited to 1024 bytes and one-byte samples are added to the buffer at a rate of 16 per second, the stored samples represent a period of approximately one minute.

Three items of information are maintained in the fixed data portion of the memory card for each circular buffer: the type of data in the buffer, the starting address of the buffer and the address of the oldest sample in the buffer. The exact format of these data items depends on the number of different types of data that may be recorded and the size of the circular buffers.

In addition to the circuitry shown in FIG. 4, it is contemplated that the call station microcomputer 414 may be coupled to a keyboard (not shown) and to a video display monitor (not shown) so that data on the patient may be viewed from and entered into both the central computer system 432 and the memory card 110 from the patient's bedside. The central computer system 432 used in the exemplary embodiment of the invention is based on a 68000 microprocessor manufactured by Motorola Semiconductor Inc.

The call station microcomputer 414 is coupled to the central nurse station microcomputer 420 via a network data link 419. The data link 419 may be, for example, a coaxial cable connection between corresponding network interface ports in the call station microcomputer 414 and the nurse station microcomputer 420. Alternatively, the nurse call station and the central nurse station 300 may be coupled through the telephone set in the patient's room. For this type of coupling, the network interface ports in each of the microcomputers 414 and 420 are configured to time-division multiplex data with voice communication when the telephone is in use. Multiple nurse call stations (not shown) may be coupled to the microcomputer 420 of the nurse station 300 via the network interconnection.

The network interconnection used to couple the nurse call station 210 to the central nurse station 300 may be a complex commercially available network interface such as that produced by Novell, Inc. or it may be a set of dedicated serial data transfer lines coupled between corresponding serial ports on the microcomputers 414 and 420.

The central nurse station 300 includes a microcomputer 420, a display driver 422, a display 322 and a keyboard 324. The microcomputer 420 used in this embodiment of the invention may be a conventional IBM Personal Computer or other compatible machine. The display driver 422, keyboard 324 and video display 322 may be any of a number of commercially available devices suitable for use with this machine.

Figure 14:
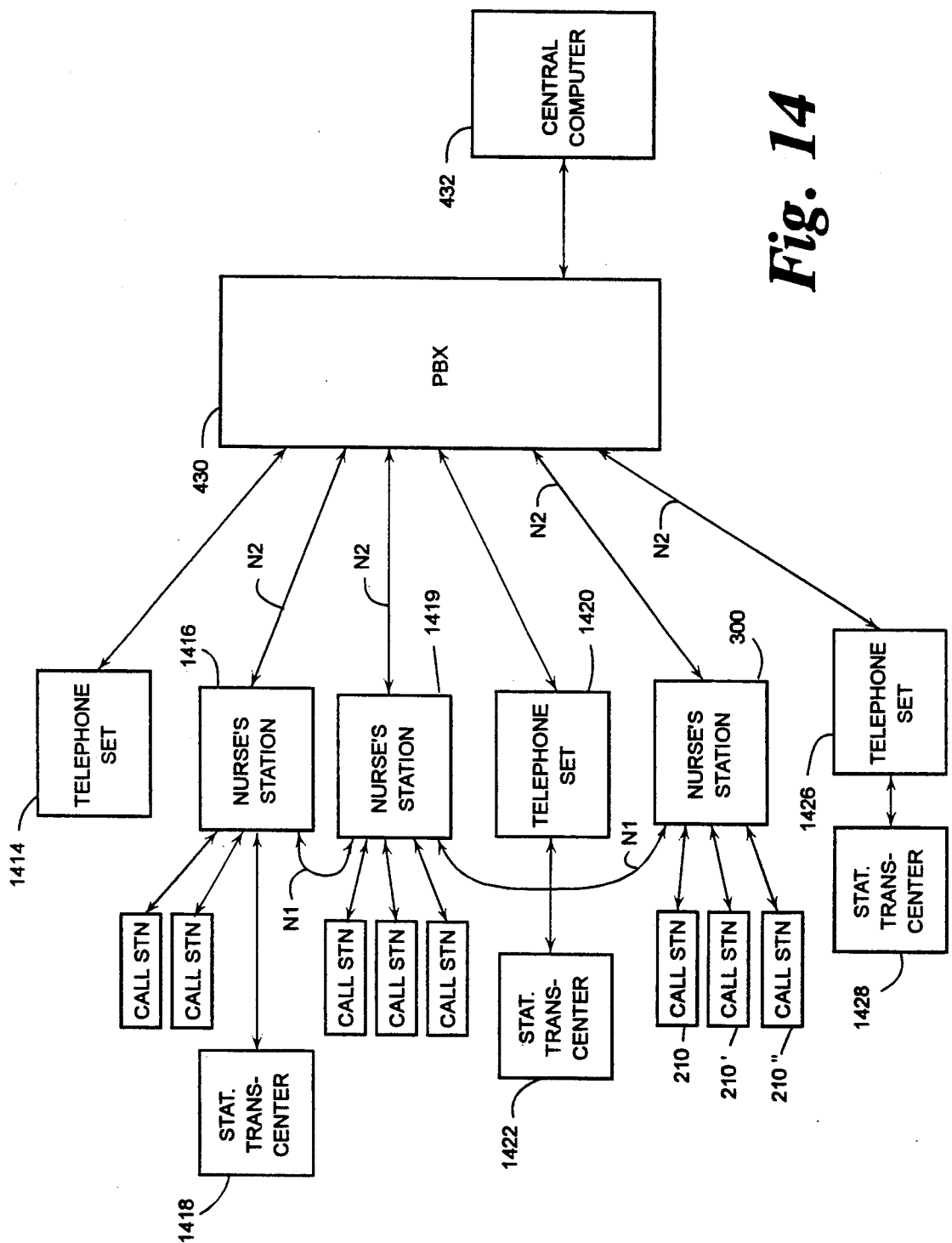
FIG. 14 is a block diagram showing an exemplary data and voice communication network suitable for use with the present invention.

The microcomputer 420 of the central nurse station 300 is coupled to the central computer system 432 of the hospital through the telephone set 310 and a private branch exchange (PBX) 430. The central nurse station 300 is one of several stations that are connected in a network configuration to the central computer system 432. The network connection to the central computer-may use a star type network in which each nurse station has an independent logical data path to the central computer. In addition, it is contemplated that the nurse stations may be coupled to each other via a ring network connection so that the failure of the central computer system does not disable communication among the nurse stations. The configuration of the networks coupling the nurse stations in the exemplary embodiment of the invention is shown in FIG. 14.

Figure 5:
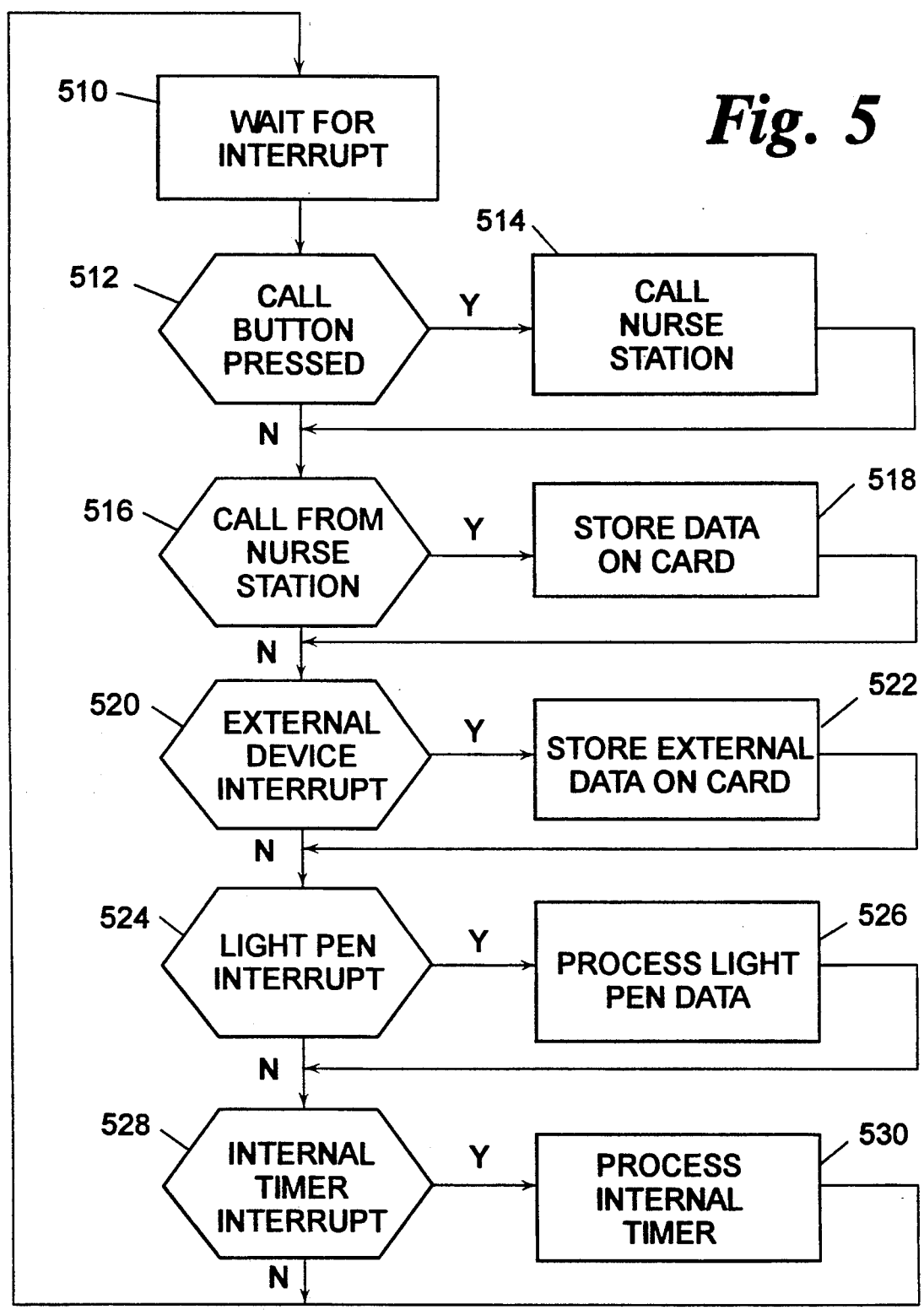

FIG. 5 is a flow-chart diagram which illustrates the main loop of the program which controls the nurse call station 210. At step 510, the microcomputer 414 in the call station 210 is in an idle state waiting for an interrupt. In this state, the microcomputer 414 may be used for other purposes, such as to provide the patient with information or entertainment. Alternatively, the microcomputer 414 may be programmed with diagnostic aids for use by the caregivers in monitoring the patient's condition.

When an interrupt occurs, the computer 414 enters an interrupt routine which checks for the occurrence of each possible type of interrupt, processes the interrupts which have been provided to the routine and returns the microcomputer 414 to its idle state.

At step 512, the interrupt routine determines if the interrupt was generated by the patient squeezing the bulb 212 or by pressing the nurse call button. If so, the step 514 is executed which performs the call nurse station function and control is transferred to step 516. The steps which implement the call nurse station function are described below in reference to FIG. 6.

After the nurse call interrupt is processed at step 514 or if the interrupt was not a nurse call at step 512, the interrupt routine, at step 516, determines if the interrupt was caused by data being provided to the microcomputer 414 from the central nurse station 300. If so, step 516 invokes step 518 to store the data provided from the nurse station 300 onto the memory car 110 and then transfers control to step 520. The steps which implement the step 518 are described below in reference to FIG. 7.

If, at step 516, it is determined that the interrupt was not caused by the receipt of data from the nurse station 300, control is transferred to step 520. Step 520 determines if the interrupt was generated by an external device, coupled to the external device input port 220 (shown in FIG. 2). As set forth above, one or more external devices may be coupled to the nurse call station 210 to store a vital sign data on the memory card 110. The interrupt detected at step 520 would occur when one of these external devices is ready to provide a sample to the call station 210.

If step 520 determines that the interrupt is from an external device, step 522 is executed to store the external data onto the card and then control is passed to step 524. The steps which implement step 522 are described below with reference to FIG. 8.

If, at step 520, it is determined that the interrupt was not generated by an external device, control is transferred to step 524. Step 524 is executed to determine if the interrupt was generated by the light pen 222. As set forth above, the light pen 222 is provided to read barcoded information from patient wrist bands, containers of prescription medicine, food trays, diagnostic images and other material that is desirably associated with a particular patient. the light pen 222 may be operated, for example, by pressing a button on the pen while the pen is dragged across the bar code and then releasing the button. The light pen interrupt would be generated when the button is released. If a light pen interrupt is detected at step 524, the interrupt routine invokes step 526 to process the light pen interrupt and then transfers control to step 528. The steps performed in carrying out step 526 are described below in reference to FIG. 9.

If, at step 524, it is determined that the interrupt was not generated by the light pen 222, control is transferred to step 528. Step 528 determines if the interrupt was caused by the internal timer of the microcomputer 414. If so, step 528 invokes a step 530 to process the internal timer interrupt. This step acts as an alarm clock to ensure that medication is administered on time and to ensure that any data which needs to be monitored at times intervals is handled properly. When the internal time has been processed, step 530 transfers control to step 510 to wait for the next interrupt. Control is also transferred to step 510 from step 528 if it is determined that no internal timer interrupt needs to be serviced.

In this description of the exemplary embodiments of the invention, reference is made to storing data into the card. If either of the memory cards 110 and 110' can undergo only a limited number of storage operations, it may be desirable to assign a buffer area in any of the microcomputers or microcontrollers coupled to the data card which acts as the card memory while the card is coupled to the device. In this instance a write operation to memory locations on the card would only be made when the card is removed from the device. At this time, the contents of the buffer may be transferred to the memory card as a block or separate write operations may be performed for those locations that have been changed while the card has been attached to the device.

Figure 6:
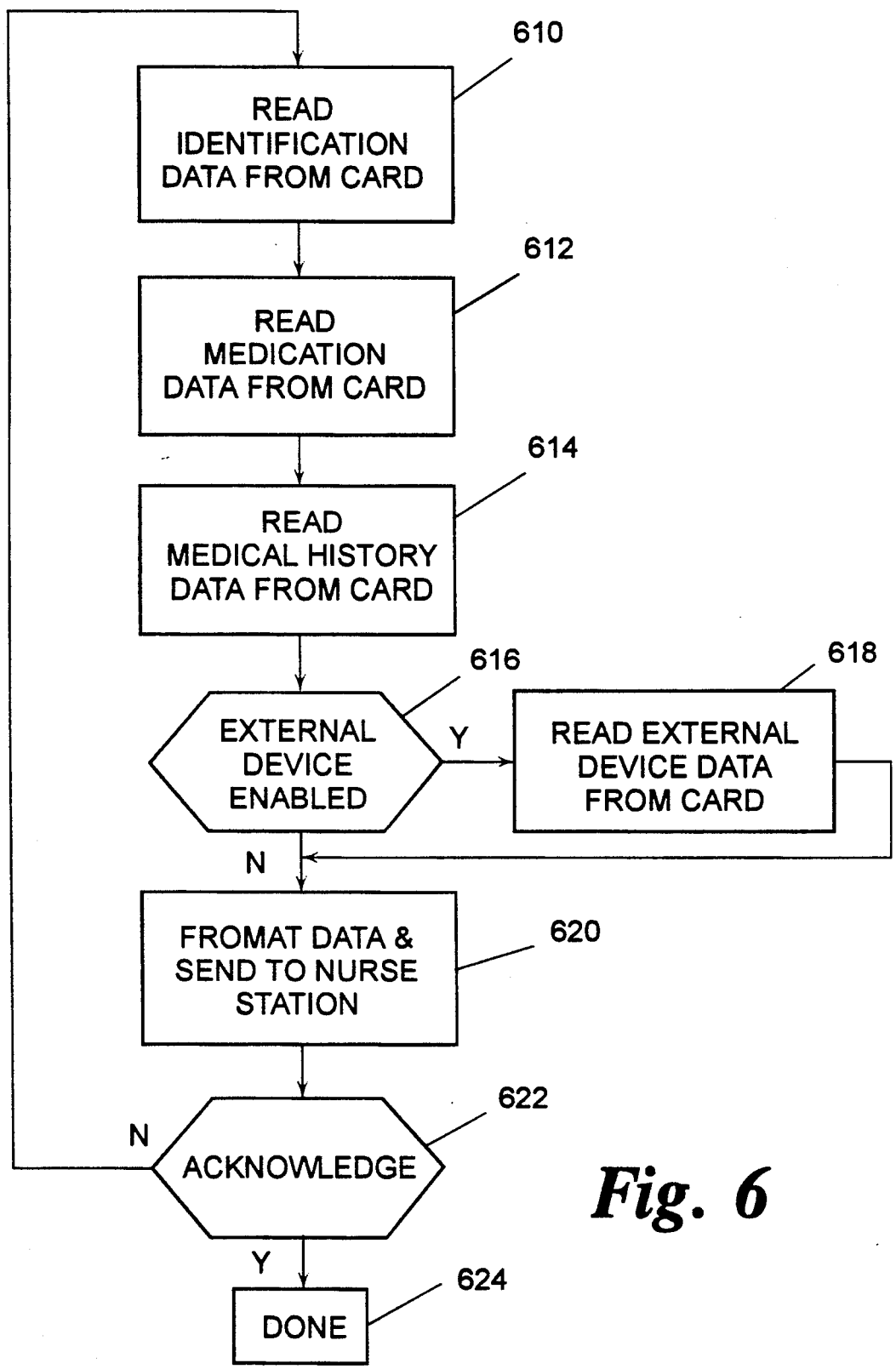

FIG. 6 is a flow-chart diagram showing details of the processing steps performed by the processor 414 in response to a nurse call interrupt. Steps 610, 612 and 614 read fixed data from the card 110 that is inserted in the nurse call station 210 as shown in FIG. 2. This data is stored in the local memory of the computer 414. At step 616, the microcomputer 414 determines if an external device is coupled to the external device input port 220, if the memory car 110 has been enabled to receive data from the device and if the device has written any data to the card. If all of these conditions are met, step 616 transfers control to step 618. The microcomputer 414, at step 618, determines the location of the data to be read and the address of the oldest sample from the fixed data portion of the memory card 110. It then transfers this data from the card into its local memory.

After step 618, or if one of the conditions fails at step 616, control is transferred to step 620. This step formats the data that has been read from the card 110 and sends it to the microcomputer 420 of the nurse station 300 via the network link 419.

At step 622, the microcomputer 414 waits for an acknowledge (ACK) response from the microcomputer 420. If a negative acknowledge (NAK) is received or if there is no response after a predetermined time-out period, the computer 414 transfers control back to step 610 and the process of extracting, formatting and transmitting the data is repeated. If the ACK is received at step 622, the call nurse station process terminates at step 624. The nurse call message will remain active at the central nurse station 300 until it is cleared by pressing the CLEAR button 218 of the nurse call station 210, as shown in FIG. 2.

Figure 7:
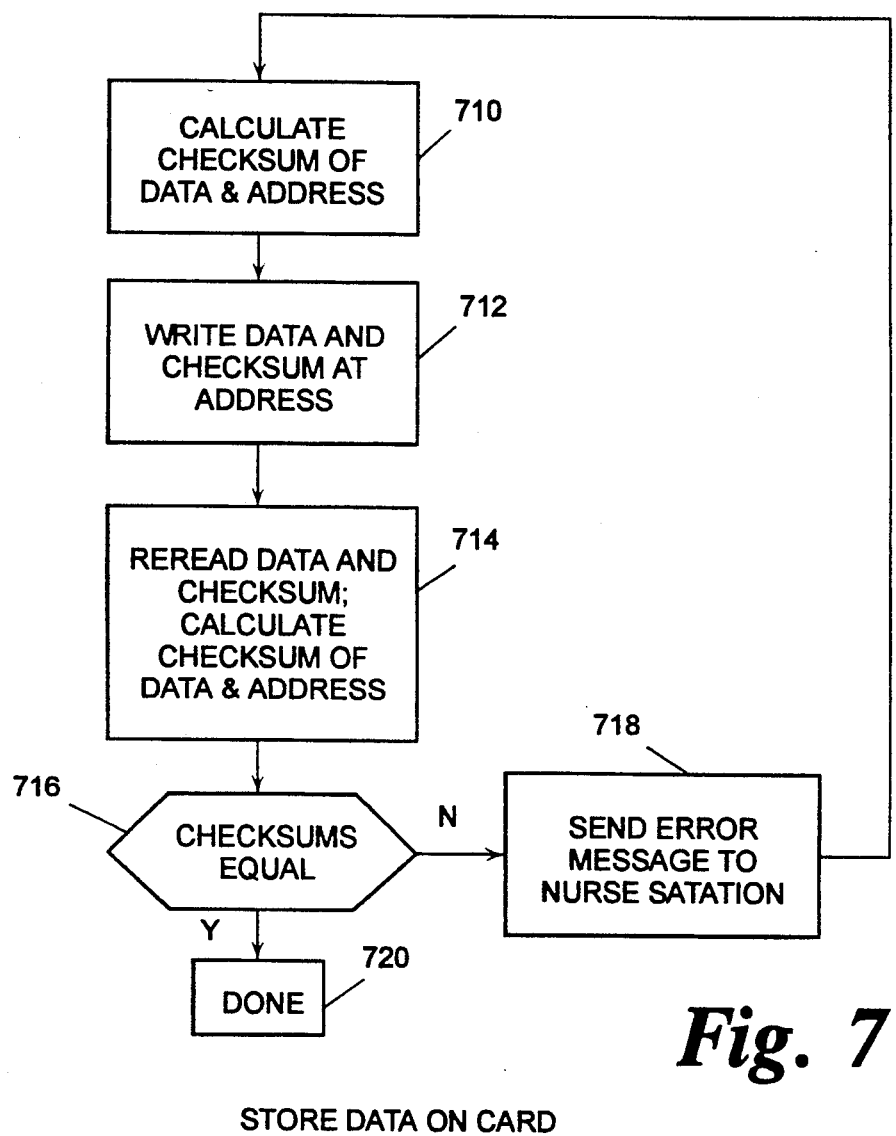

FIG. 7 illustrates the program flow of the process which stores data onto the memory card, step-518 of FIG. 5. The first step in this process, step 710, calculates a checksum of the data and the address at which the data is to be stored. At step 712, the data and the checksum are then supplied to the memory card reader/writer 412 with the starting address on the card of the first storage location to be used to hold the data. Step 712 also conditions the reader/writer 412 to write the data onto the card.

At step 714, the microcomputer 414 conditions to read the data that was just written to the card and calculates a checksum for the data and address value. Step 716 compares the checksum calculated for the original data to the checksum calculated for the retrieved data. If the checksums are not equal, the microcomputer, at step 718, sends an error message to the nurse station microcomputer 420 and transfers control to step 710 to retry the data storage operation. If, at step 716, the checksums are found to be equal, the data storage process terminates at step 720.

Figure 8:
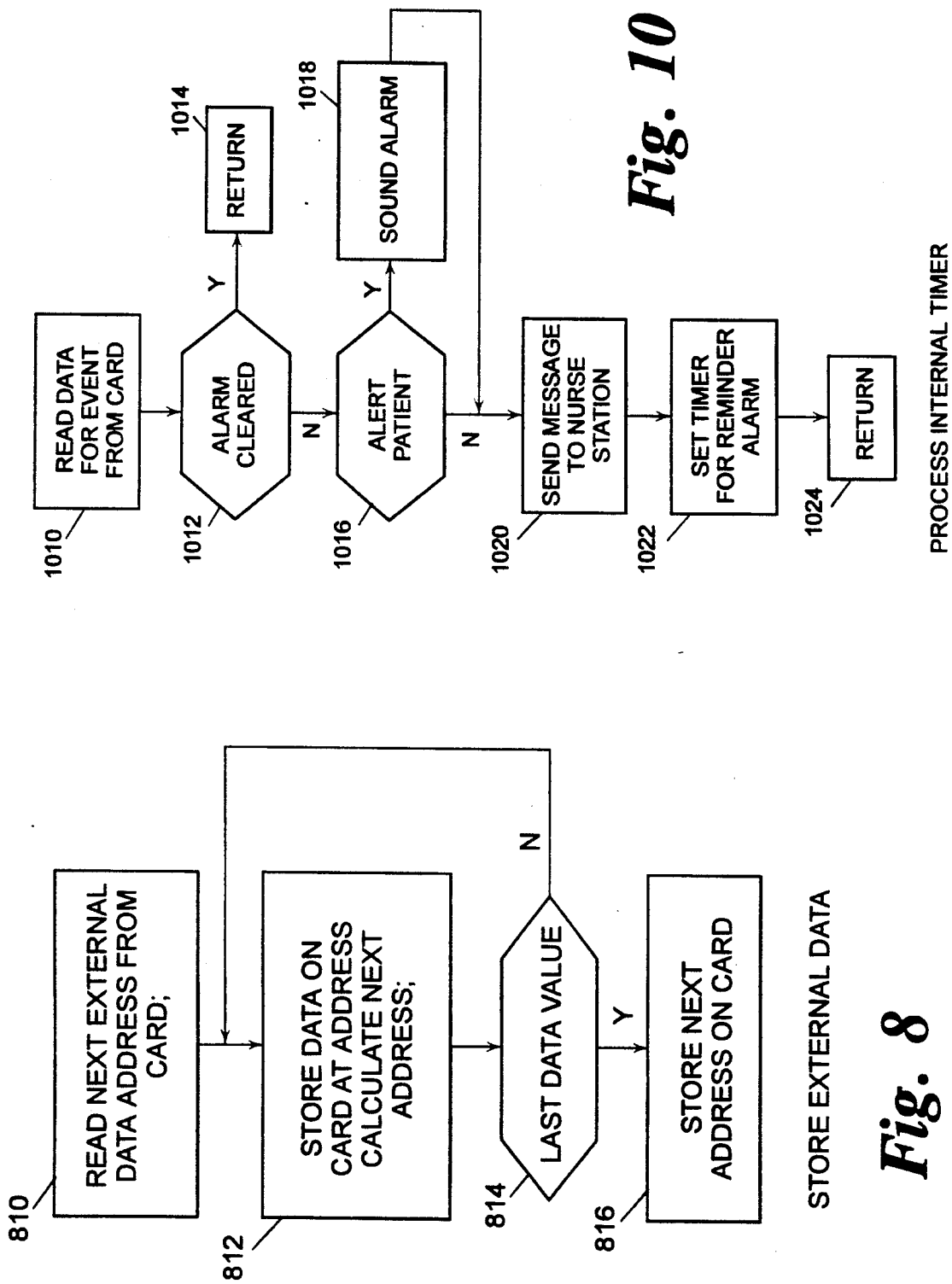

FIG. 8 is a flow-chart diagram of the process 522 of FIG. 5, which stores data from external devices onto the memory card 110. The first step in the process, 810, reads the next data address into which data is to be written from the card 110. This address is the same as the address of the oldest data item. Step 812, stores one byte of data into this address and calculates the next address. As set forth above, the address calculation uses the length of the buffer as a modulus so that the buffer appears to be a circular buffer. For example, if a buffer length of 1024 is selected and the base address of the data in the card is at BASEADR, the address calculation to obtain the next address, NXADR from the current address, CURADR may be calculated using the equation (1).

$$NXADR = BASEADR + (CURADR - BASEADR + 1) \, modulo \, 1024 \quad (1)$$

At step 814, the microcomputer 414 determines if the data item just stored was the last data item to be processed. If so, step 816 is executed in which the microcomputer 414 conditions the memory card reader/writer to store the calculated next address value in the memory card as the address of the oldest data item. Step 816 then ends the external data storage process. Otherwise, step 814 transfers control to step 812 to write the next data item onto the card.

Figure 9:
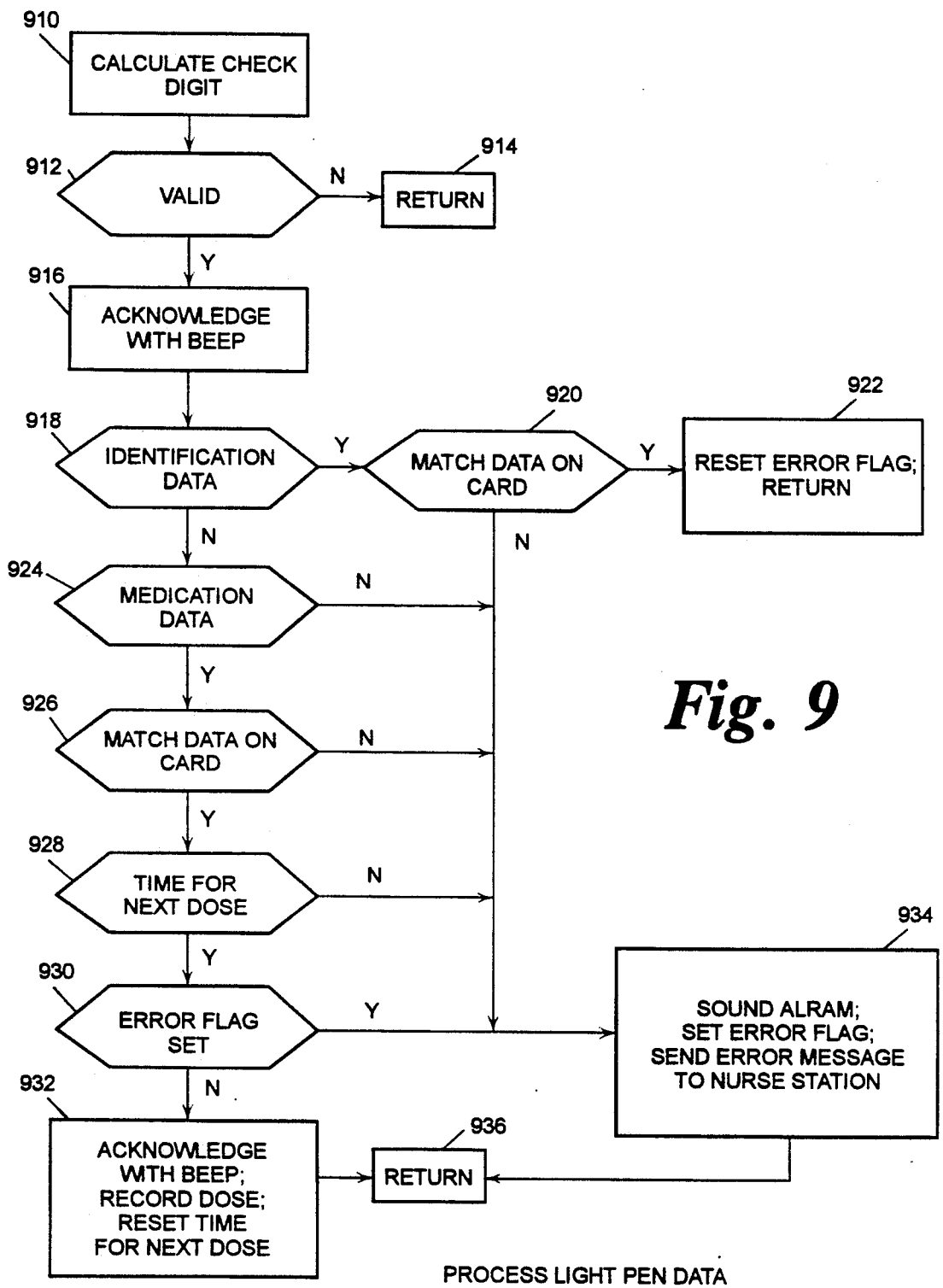

FIG. 9 illustrates the steps performed by the microcomputer 414 in processing data from the light pen 222 of FIG. 2. In the exemplary embodiment of the invention, the light pen data is provided to the microcomputer 414 via the light pen interface 416, shown in FIG. 4. This interface translates the alternating light and dark patterns sensed by the light pen 222 into a sequence of digits. Conventional bar-coded data includes a check digit, such as a cyclic redundancy code (CRC) digit, as the last digit of the data. This digit may be calculated by applying a predetermined formula to the other bar-coded digits.

In the exemplary embodiment of the invention, barcodes are used to ensure that medications, radiographic images, food trays and other material are provided to the proper patient. As an example of how the bar-codes may be used for this function, consider the administration of prescribed medication. Before giving the medication to the patient, the nurse first scans the patient arm band. The call station compares the scanned data to the identification data stored on the card. If these two codes do not match then either the patient is in the wrong bed or the wrong memory card is inserted in the call station 210.

If the codes do match, the nurse then scans the barcode on the medication container. The call station 210 compares the scanned data to medication data stored on the memory card. If a match is found, the station 210 determines when the next dose of the medicine is to be administered. If the next dose is past due or if it is due in the near future, the call station 210 records a the time at which the medication was given. If the medication is not found on the card or if it is not yet due, the station 210 sounds an alarm, for example a distinctive series of pulse tones, and sends an appropriate error message to the central nurse station. If, as set forth above, the nurse call station 210 is equipped with a display device, the error message may also be displayed on the call station display.

For radiographic images, food trays and other material that is simply to be delivered to the patient's bed, a bar-code identifying the patient is scanned from the image, tray or other material. The scanned data is then compared to the identifying data on the card. If the data is correct, the scan is acknowledged with a beep. Otherwise the alarm is sounded and an error message is sent to the nurse station 300 indicating that material has been delivered to the wrong patient.

The first step in FIG. 9, step 910, calculates the check digit using all but the last digit of the code supplied by the light pen interface 416. Step 912 then compares the calculated check digit to the last digit of the code. If the digits do not match, step 914 is executed which returns control to the main loop program shown in FIG. 5.

If, however, the check digit is found to be valid at step 912, step 916 is executed which acknowledges the receipt of the code by conditioning the nurse call station 210 to emit a beep from its speaker 214. At step 918, the microcomputer 414 determines if the code provided by the light pen interface 416 is identification data. If so, step 920 is executed to determine if the supplied code matches the code stored on the card. As set forth above, this code was entered into the card by scanning the patient's arm band during admission processing. If the scanned identification code matches the stored code at step 920, step 922 is executed which resets the error flag and returns control to the main program loop.

Otherwise, step 934 is executed. This step sounds an alarm through the speaker 214 of the nurse call station 210, sets the error flag and sends an error message to the central nurse station 300 indicating that the scanned identification data does not match the stored data.

If, at step 918, the scanned data is not identification data, step 924 is executed. Step 924 determines if the scanned data is medication data. If so, 926 is executed, otherwise, an error has occurred and control is transferred to step 934. This step operates in the same manner as set forth above, except that the error message indicates that the scanned data was neither identification data nor medication data.

Step 926 determines if the scanned medication matches any of the medication data stored on the memory card 110. If a match is found, step 928 is executed, otherwise an error has occurred and step 934 is executed with an error message indicating that the medication has not been prescribed for the patient.

In step 928, the microcomputer 414 compares the current time, as derived from its internal time of day clock, to the stored time for the next dose of the medication. This time value is stored in the card 110 as a part of a multi-value record for the medication information. Each prescribed medication is entered in the card 110 as a separate medication record. If the next-dose time has passed or if it is in the near future, for example, 15 minutes from the present, step 930 is executed. Otherwise, an error has occurred and step 934 is executed with an error message indicating that the medication is being provided at the wrong time.

Step 930 checks the error flag. This flag is set in step 934 if any error occurs and is reset in step 922 when the scanned identification data is found to match the patient. The test in 930 ensures that erroneous identification data is not ignored. If the error flag is set at step 930, then an error that occurred during a previous attempt to administer medication has not been cleared. In this instance, step 934 is executed with an error message indicating that a previous error has not been cleared.

If, at step 930, the error flag is reset, step 932 is executed. This step conditions the call station 210 to emit an acknowledging beep, disables any internal timer interrupt that may be set for this medication dose, records the current time in the medication record to indicate that the medication has been administered and calculates the time for the next dose. The next-dose time is also stored in the medication record on the memory card 110 and an internal timer interrupt is set for this next dose time. After step 932 and after step 934, the process which reads the light pen data is complete and control is returned to the main loop program at step 936.

FIG. 10 illustrates the program flow of step 530 of FIG. 5, which processes the internal timer interrupts from the microcomputer 414 of the nurse call station. In the exemplary embodiment of the invention, the timed event, for example, the next-dose time in a medication record, is stored on the card at a known location. Step 1010 reads the event data from the card, using the address that was stored with the timer interrupt request. Step 1012 compares the stored time to the current time and checks an alarm cleared flag to determine if the alarm is no longer necessary. If step 1012 determines that the alarm has been cleared, control is returned, at step 1014, to the main program loop of FIG. 5.

If the alarm has not been cleared at step 1012, step 1016 is executed to determine if the patient is to be alerted or if only the central nurse station is to be alerted. If the patient is to be alerted, step 1018 is executed which conditions the call station 210 to emit an audible alarm through the speaker 214. Whether or not the patient is to be alerted, step 1020 is executed to send an alarm message to the central nurse station. In the exemplary embodiment of the invention, the text of the alarm message is determined from a code stored with the timer interrupt data on the memory card 110. This code is used to index a table of alarm messages stored in read-only memory (ROM) (not shown) in the call station microcomputer 414.

After step 1020, the microcomputer 414 executes step 1022 to set a reminder alarm for a predetermined time, for example, five minutes after the initial alarm. This reminder alarm is handled in the same manner as any other internal timer interrupt. Any outstanding reminder alarms may be cleared by pressing the CLEAR button 218 on the call station 210.

The discussion above has centered on the use of the invention for patients in a hospital. Since a hospital patient spends a large percentage of time in his bed, the interface between the personal database and the hospital computer system can be a fixture in the patient's room. For reasons set forth below, it is desirable to extend the use of the invention to caregivers at the hospital. Caregivers, however, are more mobile and would not be adequately served by an immobile interface.

FIGS. 11a and 11b illustrate a mobile interface suitable for use with a memory card of the type described above. This interface includes a radio frequency transceiver which can both transmit data to and receive data from a group of stationary transceivers located at various places in the hospital. As set forth in detail below, the mobile interface shown in FIGS. 11a and 11b can also read data from and write data to a memory card.

The database interface shown in FIGS. 11a and 11b is a card holder which converts a memory card 110' into an identification badge. The interface includes a clear plastic front piece, 1110, which protects the memory card 110' and through which information printed on the front of the card may be seen. The front piece 1110 is attached to a base 1112 which includes all of the electronic components of the database interface. The base includes a fastener 1116, shown in the exemplary embodiment as a safety pin, which is used to attach the card holder to an article of clothing, such as the sleeve or pocket of a nurse's uniform. The memory card 110' is inserted into a slot 1114 in the base 1112 to make both physical and electrical contact with the base 1112.

In addition to the circuitry used to read data from and write data to the memory card 110', the base unit 1112 includes a push-button switch 1118 through which the person wearing the badge may signal a response to the stationary system, and a speaker 1120 through which the wearer may be notified of an incoming message.

Figure 12:
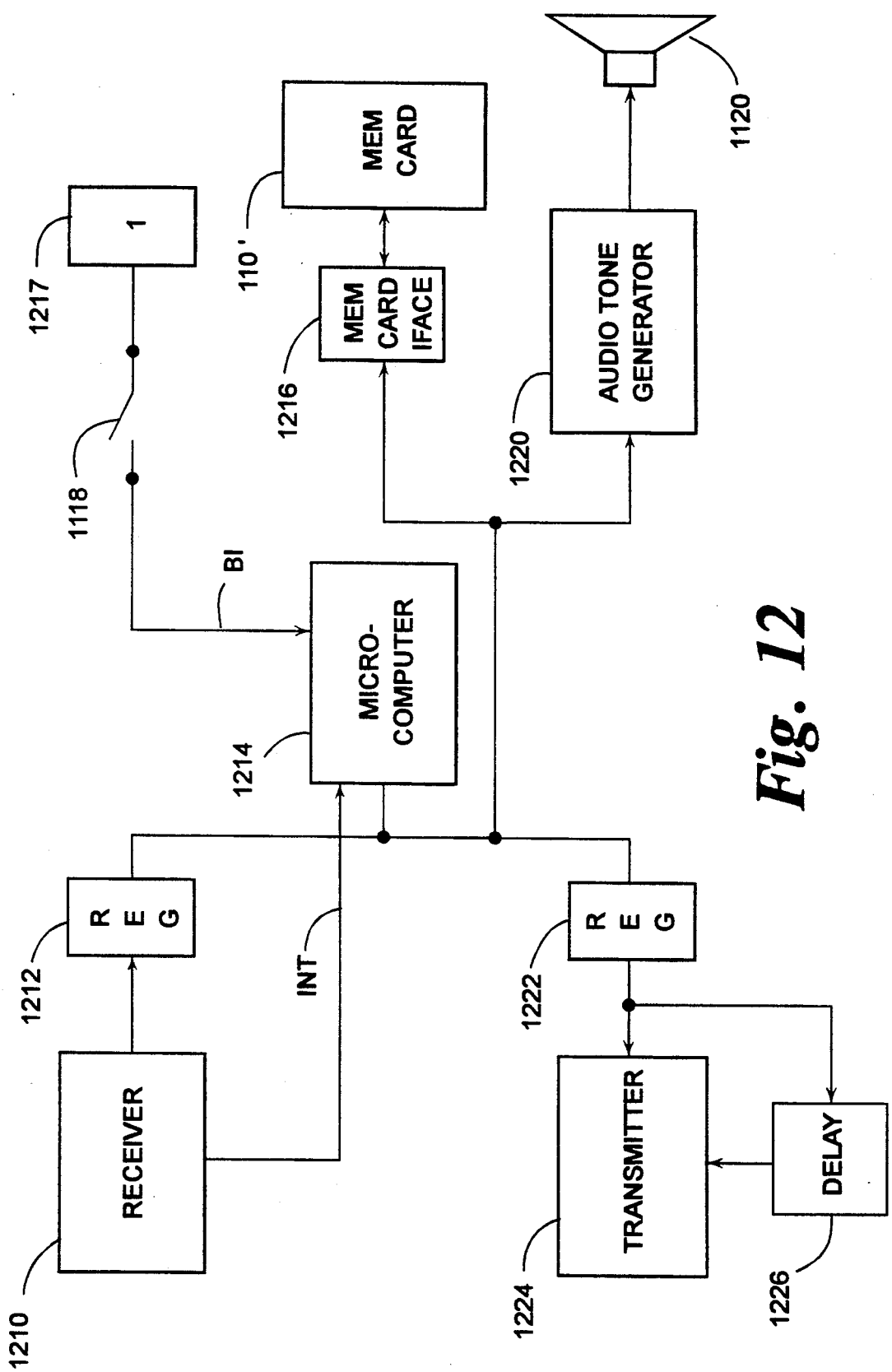
FIG. 12 is a block diagram showing the functional connectivity of the portable transceiver shown in FIGS. 11a and 11b.

FIG. 12 is a block diagram that illustrates the functional structure of the electronic circuitry in the base 1112 of the badge-holder database interface. For the sake of simplicity, the power supply has been omitted from FIG. 12. In the exemplary embodiment, power is provided by a standard replaceable lithium battery. Signals from the fixed transceivers are received by the badge via the receiver 1210. The receiver 1210 stores each data value it provides into a register 1212. In addition, the receiver 1210 notifies a microcomputer 1214 that a value has been received by an interrupt line INT. Responsive to this interrupt, the microcomputer 1214 reads the value from the register 1212 and stores the value in its local memory (not shown). When the microcomputer has received a set of values which constitute a message, it performs the functions indicated by the message. The microcomputer 1214 may be any one of a number of commercially available microcontrollers, such as the 80C49 manufactured by Intel Corporation, coupled to ROM program storage (not shown) and RAM data storage (not shown).

The functions performed by the microcomputer 1214 may include providing an address to a memory card interface 1216 to read data from the memory card 110, providing data and an address to the interface 1216 to write data into the memory card 110', conditioning an audio tone generator 1220 to produce an audio signal from the speaker 1120, or storing a value into the register 1222 and then conditioning the transmitter 1224 to broadcast the data value to the network of fixed transceivers.

Each badge transmitter 1224 is coupled to a programmable delay element 1226 which delays the start of data transmission by a preprogrammed amount of time. Each badge transmitter is programmed with a respectively different delay value. This time delay ensures that messages sent from multiple badges do not overlap.

Also included in the badge circuitry is the push-button switch 1118, through which a source of logic-one value, 1217, may be momentarily coupled to an interrupt line, BI, of the microcomputer 1214. In response to this interrupt, the microcomputer 1214 sends identifying information, read from the memory card 110' and either an emergency alert message or an acknowledge message. The operation of the circuitry shown in FIG. 12 in the hospital environment is described below with reference to FIGS. 13-16.

In the exemplary embodiment, the transmitter and receiver components of the badge holder are radio-frequency devices, operating at frequencies of approximately 300 MHz and 500 KHz, respectively. Radio frequency transmitters and receivers suitable for use in the badge holder are available from Dallas Semiconductor Inc. It is contemplated that other transmitter and receiver components may be used, for example, the infrared transmitter and receiver of the PLS-4000 personnel locating system available from TELOC, Inc.

As set forth above, the present badge transceiver has advantages over the prior art badge transceivers in that the identification information transmitted by the present badge is contained in the removable memory card 110', while in the prior art badges this information is programmed into a memory element which is not easily removable. Thus, if a particular badge unit fails, a new badge may be configured by removing the memory card from the failed badge holder and inserting it into a new badge holder. In addition, the present badge transceiver can store data transmitted from the network of fixed transceivers. The prior art transceivers do not have this capability.

Figure 13:
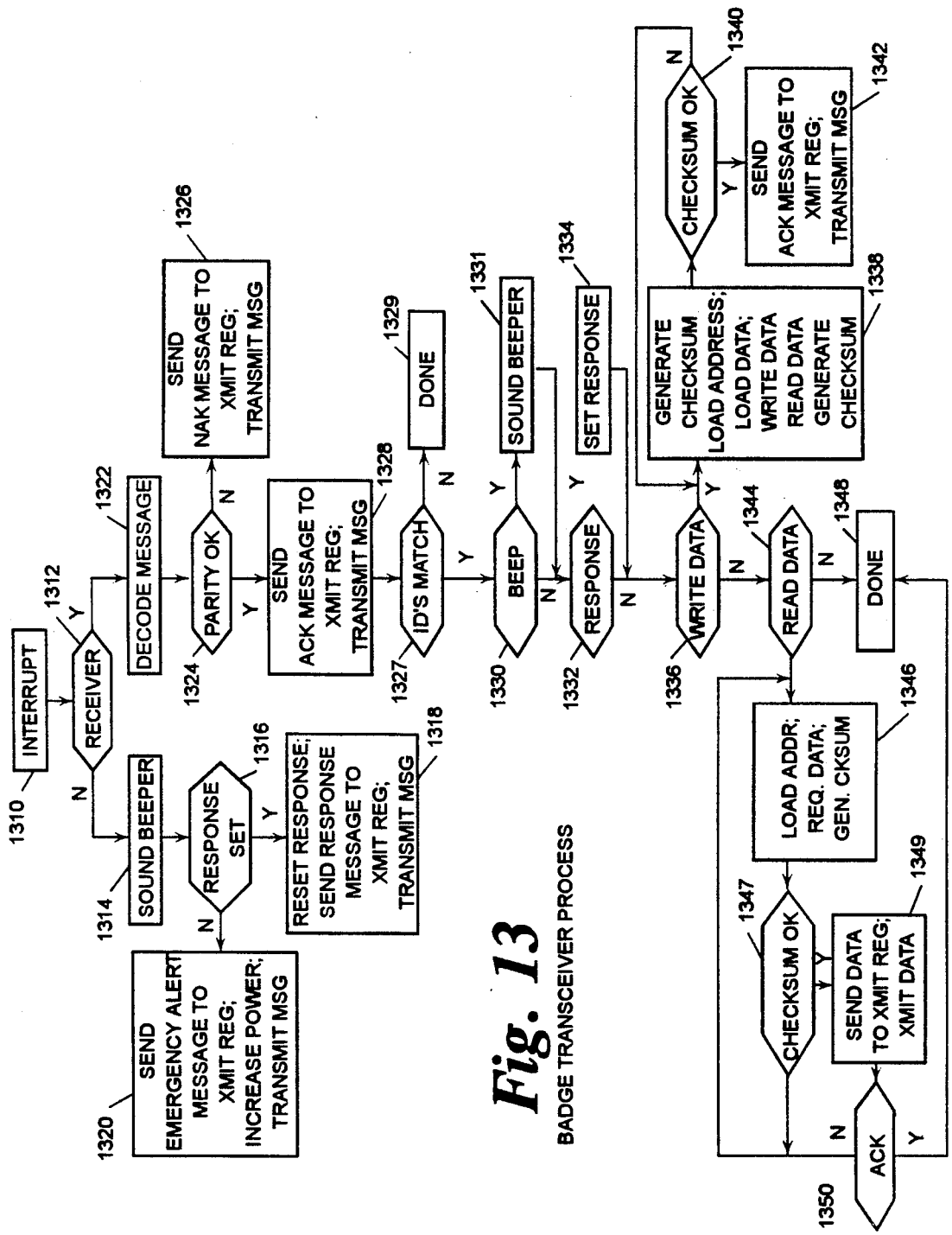
FIG. 13 is a flow-chart diagram which illustrates the operation of the portable transceiver unit shown in FIG. 12.

FIG. 13 is a flow-chart diagram which illustrates the operation of the badge transceiver shown in FIGS. 11 and 12. The badge transceiver is activated by an interrupt at step 1310. The interrupt may either be from the receiver 1210 or from the push-button switch 1118. If, at step 1312, it is determined that the interrupt was generated by the switch 1118, the microcomputer 1214, at step 1314, conditions the audio generator 1220 to provide a pulse tone signal to the speaker 1120. This tone serves as audio feedback letting the wearer know that the badge circuitry has sensed the closing of the switch 1118.

At step 1316, the microcomputer 1214 determines if a prior message received by the badge transceiver required a response. If so, step 1318 resets the response indicator, provides the appropriate response message to the transmit register 1222 and conditions the transmitter 1224 to transmit the message. If, at step 1316, it is determined that no response is required,-then the wearer is assumed to be signalling an emergency alert. In this instance step 1320 is executed which conditions the microcomputer 1214 to send an emergency alert message to the transmit register 1222 and to increase the level of power applied to the transceiver and to condition the transmitter 1224 to transmit the register.

In order to reduce the number of accidental emergency alert messages, it may be desirable to program the microcomputer 1214 to require that the switch 1118 be pressed in a pattern, for example, three times within a 10 second interval to signal an emergency alert. After the message is transmitted in either step 1318 or step 1320, control is transferred to step 1310 to await the next interrupt.

If, at step 1312, it is determined that the interrupt was caused by the receiver 1210, step 1322 is executed to store and decode the received message. When the message has been stored, step 1324 is executed to determine if the data was received without parity errors. If parity errors are detected, step 1326 is executed. This step sends a NAK message to the network of stationary transceivers, conditioning the stationary transceivers to transmit the data again. After step 1326, the microcomputer 1214 transfers control to step 1310 to await the next interrupt.

When a message is received without parity errors, step 1328 is executed to send an ACK message to the network of stationary transceivers, acknowledging that the message has been received. Step 1327 then compares the identifier from the decoded message to the identification data stored on the memory card 110'. If the two identifiers do not match, then the message was meant for another card. In this instance, step 1329 returns control to step 1310 to await the next interrupt.

This step filters out messages which were meant for other badges. In the exemplary embodiment of the invention, the step 1327 matches the transmitted identification number both to the identification number extracted from the memory card 110' and to a null identification number that is used to identify messages that are intended to be received by all badges.

If, at step 1327, the identifiers are found to match, step 1330 is executed. Step 1330 determines from the message if the wearer should be notified that a message has been received. If so, at step 1331, the microcomputer 1214 conditions the tone generator 1220 to emit a pulse tone signal through the speaker 1120.

The next step in the process, step 1332, examines the received message to determine if a response is expected. If so, step 1334 is executed to set the response indicator. This indicator is examined and reset by steps 1316 and 1318, described above.

After determining whether a response is expected, the program controlling the badge transceiver determines, at step 1336, if the received message contains data to be written into the memory card 110'. If so, step 1338 is executed. This step calculates a checksum for the data to be written into the card, loads the starting address into the memory card interface 1216, loads the data into the memory card interface and conditions the interface 1216 to write the data onto the card. Step 1338 then conditions the interface 1216 to read the data that was just stored and to generate a second checksum.

At step 1340, the original checksum and the second checksum are compared. If they do not match, control is transferred to step 1338 to retry the write operation. If the checksums match at step 1340, step 1342 is executed. This step sends an ACK message to the network of fixed transceivers, indicating that the data has been successfully stored.

If, at step 1336, data is not to be written into the memory card 110′, step 1344 is executed to determine if data is to be read from the memory card 110′. If data is to be read, step 1346 is executed which loads the address into the memory card interface 1216 and then conditions the memory card interface to read the data at that address. The data that is read includes a checksum. At step 1346, the microcomputer 1214 calculates a second checksum using all of the bytes read from the memory card 110′ except the checksum byte. At step 1347, the read checksum is compared to the calculated checksum. If a difference is detected, the program branches to step 1346 to retry the read operation. Otherwise, control is transferred to step 1349 to transmit the data and the checksum to the fixed transceiver network. At step 1350, the microcomputer 1214 waits for an ACK response indicating that the data has been received. If no response is received within 2 seconds or if a NAK response is received, control is transferred to step 1346 to retry the read and transmit operations.

After a successful data transmission or if, at step 1344, it is determine that no data is to be read, control is transferred to step 1310 to await the next interrupt, as indicated by step 1348.

As set forth above, the badge transceiver is used, in this embodiment of the invention as a data link between the personal database implemented in the memory card 110′ and the central computer system. The other part of this data link is the network of stationary transceivers located at fixed positions around the hospital. FIG. 14 is a block diagram showing the data link between the network of stationary transceivers, the central nurse stations, the nurse call stations and the central computer system 432.

The stationary transceivers used in the exemplary embodiment of the invention are coupled to respective telephone sets through which the stationary transceivers are connected to the PBX 430, which is in turn, connected to the central computer 423. In the simplified exemplary configuration shown in FIG. 14, a telephone set 1414, two telephone sets 1420 and 1426 coupled to stationary transceivers, and three telephone sets coupled to central nurse stations 1416, 1419 and 300 are shown connected to the PBX 430. As set forth above, each line between the PBX 430 and a telephone set includes an independent logical data path which may be used to connect data processing apparatus connected to the telephone sets in a network with the central computer 432. This data path may be a separate pair of conductors or it may be a virtual path formed by time-division multiplexing the data to be transferred with audio frequency data from the telephones. Both of these schemes are well known to those of ordinary skill in the art of designing telephone systems. An exemplary PBX which supports this type of data communication is the IDS 432 family of products available from Executone Informations Systems Inc.

In addition to the data communications network N2 through the PBX 430, the nurse stations 1416, 1419 and 300 are coupled together by a ring network N1. This network serves as a backup to the network N2. In the event of a failure of either the PBX 430 or the central computer 432, data communications among the central nurse stations would occur through the network N1.

In the exemplary embodiment of the invention, each of the stationary transceivers 1418, 1422 and 1428 is responsive to commands from the central computer 432 to send messages to and receive data from the various badge transceivers. Each stationary transceiver includes circuitry which automatically performs all of the steps needed to ensure that the command from the main computer is carried out and that the data was delivered without corruption.

Figure 15:
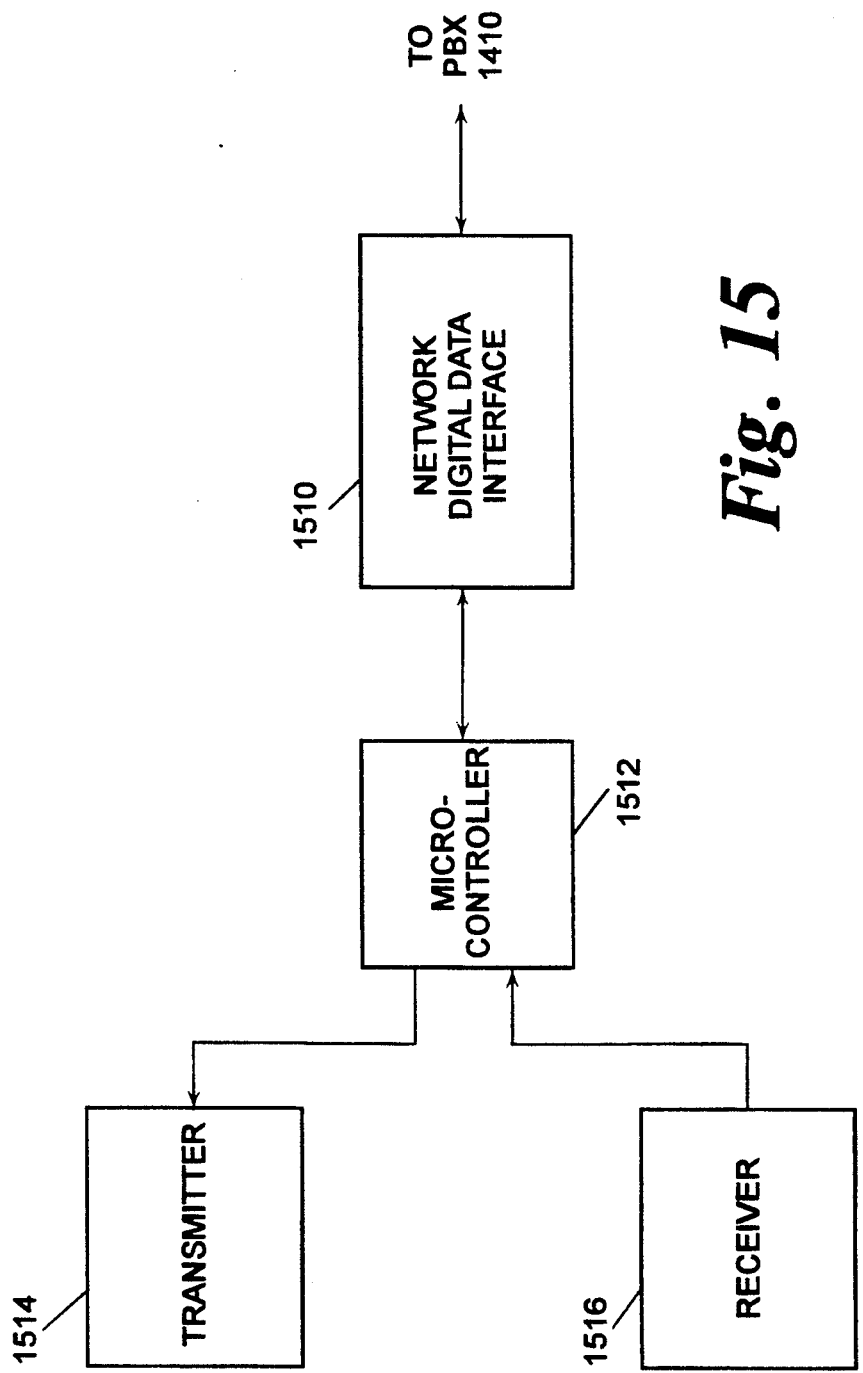
FIG. 15 is a block diagram showing details of the transmitter-receiver units shown FIG. 14.

FIG. 15 is a block diagram showing the functional structure of a stationary transceiver. In addition to a transmitter 1514 and a receiver 1516, the transceiver includes a microcontroller 1512 and a digital data interface 1510 through which the transceiver is coupled to the PBX 1410. An exemplary stationary transceiver suitable for use as the unit shown in FIG. 15 is the DS6068A unit available from Dallas Semiconductor Inc. Alternatively, an infrared device such as those used in the PLS-4000 Personnel Locating System available from TELOC Inc. may be used for the stationary transceiver. The network digital data interface 1510 provides a digital data connection to the PBX 1410 through one of the telephone sets. The type of unit used depends on the network connectivity available through the PBX. In the exemplary embodiment of the invention, a standard communications interface, such as an IEEE 488 bus is used with an IDS 432 PBX, available from Executone Information Systems.

The stationary transceiver shown in FIG. 15 includes a microcontroller 1512. This unit includes a simple microprocessor (not shown), a ROM program store (not shown) and a small RAM (not shown) for holding data and temporary results.

Figure 16A:
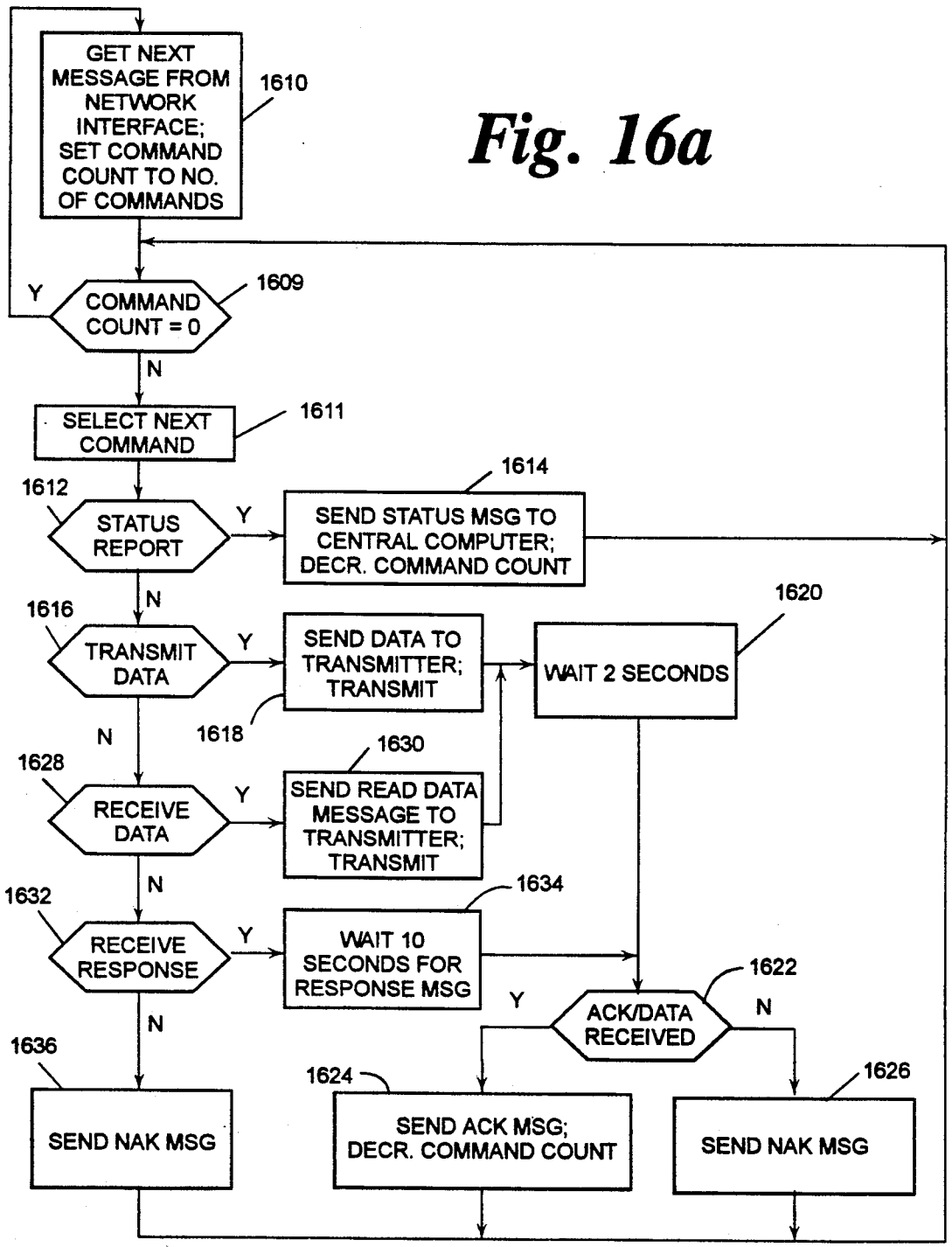

FIG. 16a is a flow-chart diagram which illustrates the process steps performed by the program that controls the microcontroller 1512. As set forth above, the stationary transceivers 1418, 1422 and 1428 are programmed to carry out commands provided by the central computer system. These commands include: a status request command for which the stationary transceiver sends an indication of its status to the main computer, a transmit data command for which the stationary transceiver transmits data provided with the command, and a receive data command for which the stationary transceiver expects to receive data from a badge transceiver. Multiple commands may be issued at a single time. For example, the central computer may broadcast a message to all stationary transceivers to locate the memory card of a particular individual. This message would include a transmit data command, which conditions the stationary transceivers to broadcast the identification number of the individual, and a receive data command, which conditions the transceivers to wait for a response from the badge holder that is coupled to the card which is to be located.

In step 1610 of FIG. 16a the command message is received from the central computer 432 via the data communications network N2 and the network interface 1510 and the number of commands in the message is stored in memory location COMMAND COUNT. This memory location serves as a pointer to the commands in the message.

Step 1609 determines if any commands in the message have not been executed. If unexecuted commands exist, then at step 1611, the next command is selected from the message. At step 1612, the microcontroller 1512 determines if this command is a status request command. If so, step 1614 is executed. This step sends a status message to the central computer 432 and decrements COMMAND COUNT so that it points to the next command. The status message may include, for example, information identifying the stationary transceiver and its location, and the numbers of ACK and NAK messages both sent by and received by the stationary transceiver. The relative numbers of ACK and NAK messages provide an indication of the condition of the stationary transceiver. After step 1614 control is transferred to step 1609 to extract the next command from the received message.

If, at step 1614, the selected command is not a status request, then step 1616 is executed. This step determines if the command is a transmit data command. If so, at step 1618, the data to be transmitted is sent to the transmitter 1514 and the transmitter is conditioned to broadcast the data. At step 1620, the microcontroller 1512 waits two seconds for an ACK message from one or more badge transceivers, indicating that the message has been received.

If, at step 1622, an ACK is received during the two second interval, the microcontroller 1512, at step 1624, sends an ACK message to the central computer 432, decrements the COMMAND COUNT to point to the next command and transfers control to step 1609 to retrieve the next command from the message. Otherwise, at step 1626, the microcontroller 1512 sends a NAK message to the central computer and branches to step 1609 to retry the current command. In this embodiment of the invention, the central computer 432 is programmed to allow a fixed number of retries (consecutive NAK messages) and then to retransmit the command message to the stationary transceiver.

At step 1616, if the selected command was not a transmit data command, step 1628 is executed to determine if it is a receive data command. If so, the microcontroller 1512 sends a read data message to the transmitter 1514 and conditions the transmitter to broadcast the message. Step 1630 then transfers control to step 1620, described above.

Steps 1620, 1622, 1624 and 1626 operate in the same manner for the receive data message as for the transmit data message except that step 1624 sends the data to the central computer 432 and an ACK message to the badge transceivers, while step 1626 sends NAK messages to both the badge transceivers and the central computer 432. The microcontroller 1512 does not check for parity errors or checksum errors in the received data. These checks are performed at the central computer when it receives the data.

If step 1628 determines that the command is not a receive data command, then step 1632 is executed to determine if it is a receive response command. If so, the microcontroller 1512 sets an internal memory location, RESPONSE to indicate that a response is expected and stores information identifying the person from whom the response is expected in an associated memory location. Next, step 1632 decrements COMMAND COUNT. No message is sent to the badge transceiver in this case since the request for a response is encoded in the transmit data or receive data message sent at steps 1616 or 1628, respectively. After step 1634 is executed, control is transferred to step 1609 to select the next command to be executed. The process by which the response is handled is described below with reference to FIG. 16b.

If, at step 1632, the command is not a receive response command, then it is an unknown command. In this instance, the microcontroller 1512 sends a NAK message to the central computer 432, decrements the command count and then branches to step 1609 to get the next command.

The process illustrated in FIG. 16a runs on the microcontroller 1512 in a continuous loop. This process may be interrupted by a signal received from one of the badge transceivers. In this instance, the receiver 1516 of the stationary transceiver causes an interrupt in the microcontroller 1512. At step 1650 of FIG. 16b, the interrupt is sensed. At step 1652, the memory location RESPONSE is tested to determine if a response is expected and that the identification information received with the interrupt matches that of the badge which is to respond. If both conditions are met in step 1652, step 1656 is executed. This step resets the memory location RESPONSE, sends a response message to the central computer 432, providing the identification number and status of the responder, and then sends an ACK message to the badge transceiver.

If, at step 1652, the memory location RESPONSE is not set or if the responder is not the individual that was expected to respond, then the interrupt is not a response but an emergency alert request. In this instance, step 1654 is executed. This step sends an emergency alert message to the central computer. This message includes the identifying information from the badge that initiated the alert and the location of the stationary transceiver which received the emergency alert message.

Figure 17B:
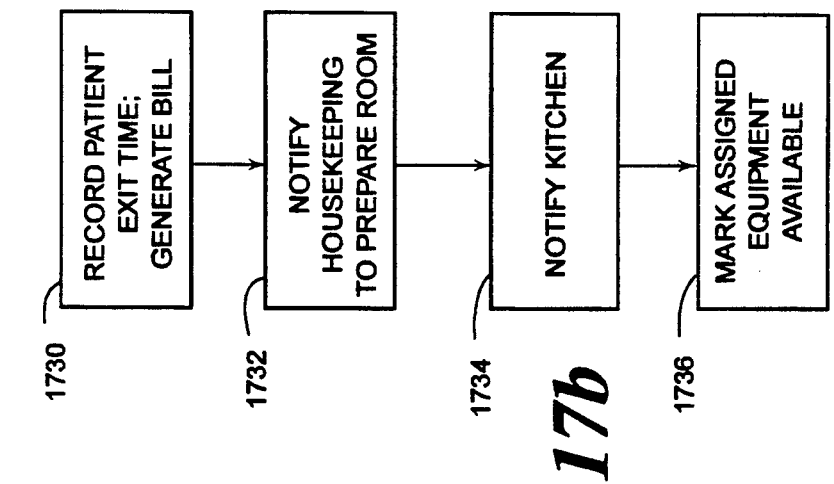
FIGS. 17a and 17b flow-chart diagrams which illustrate the-handling of patient entry and patient exit using a hospital monitoring system that includes an embodiment of the present invention.
Figure 17A:
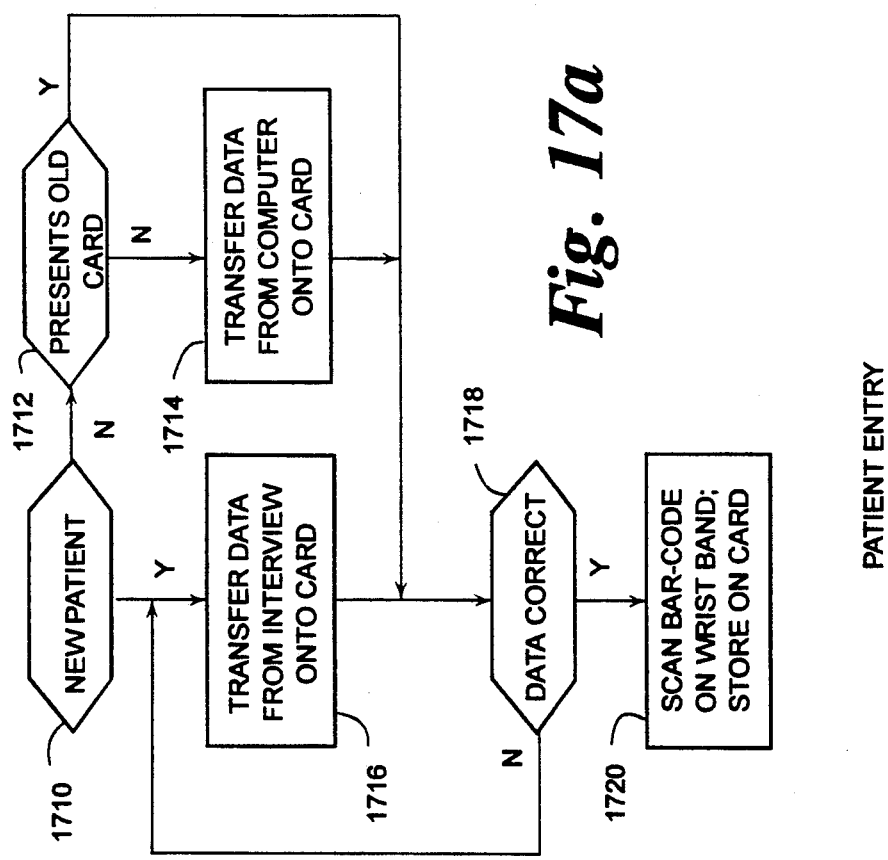

The discussion of FIGS. 1–16b above has described various components of a distributed processing network in which information on individuals and important equipment is stored on a personal database that is kept in close proximity to the individual or equipment. FIGS. 17a through 17d illustrate four exemplary functions that may be performed using this network. FIGS. 17a and 17b describe steps performed when the patient enters and leaves the hospital, FIG. 17c describes a process for locating equipment and personnel, and FIG. 17d describes a process for automating the assembly of teams of specialists to handle an emergency situation such as a "code blue."

At step 1710 of FIG. 17a, when a patient enters the hospital he may already have been issued a memory card 110. If so, at step 1712, he may have the card in his possession, in which case he presents it, or he may not have the card. If he does not have the card, step 1714 is executed which transfers an image of the card data as of the time the patient left the hospital, onto a new card. This stored data may be maintained in auxiliary data storage, such as a cartridge tape, coupled to the central computer 432. If, at step 1710, the patient has not been assigned a card, he is interviewed and, at 1716, the data from the interview is stored on a memory card. At step 1718, data on the card is printed so that the patient may examine and correct it. If any corrections are needed, step 1718 branches to step 1716 to enter the corrections.

After step 1718, when the patient has a card and the data on the card is correct, step 1720 is executed. In this step, an identifying wrist band, such as the band 140 described above in reference to FIG. 1d, is physically attached to the patient and the bar-code on the band is read and stored into a memory location on the memory card.

When the patient is taken to his room, the card is inserted into the nurse call station 210 as set forth above in reference to FIG. 2. When the patient's food trays are prepared in the hospital kitchen, the central computer 432 is first checked to determine if the patient is still in his room and if his diet has been changed. This information is obtained directly from the memory card 110. When the tray is prepared, a sticker containing the patient's bar-code identification information and room number is attached to the tray. When the orderly delivers the tray, he scans the bar-code on the patient's wrist and the bar-code on the tray using the light pen at the nurse call station located near the patient's bed. If the bar-codes match, the call station 210 emits an acknowledging beep and notifies the central computer that the tray has been delivered. If the bar-codes do not match, the call station 210 emits an alarm tone. In this instance, the orderly may take the tray to the closest nurse station to determine what type of error occurred and how it may be corrected. The same procedure could be used to deliver radiographic images or medical test results to a patient's bedside.

In FIG. 17b, when a patient leaves the hospital, he presents his card at the administration desk and the card is coupled to the central computer 432 which, at step 1730, records the exit time and generates billing information. At steps 1732 and 1734, the central computer notifies housekeeping and the hospital kitchen to prepare the bed for the next patient and to make no more food trays for the patient. Step 1736 checks for any equipment that was assigned to the patient and sends a message to the memory cards 110', coupled to badge transceivers which are attached to the equipment, marking the equipment as available.

Figure 17C:
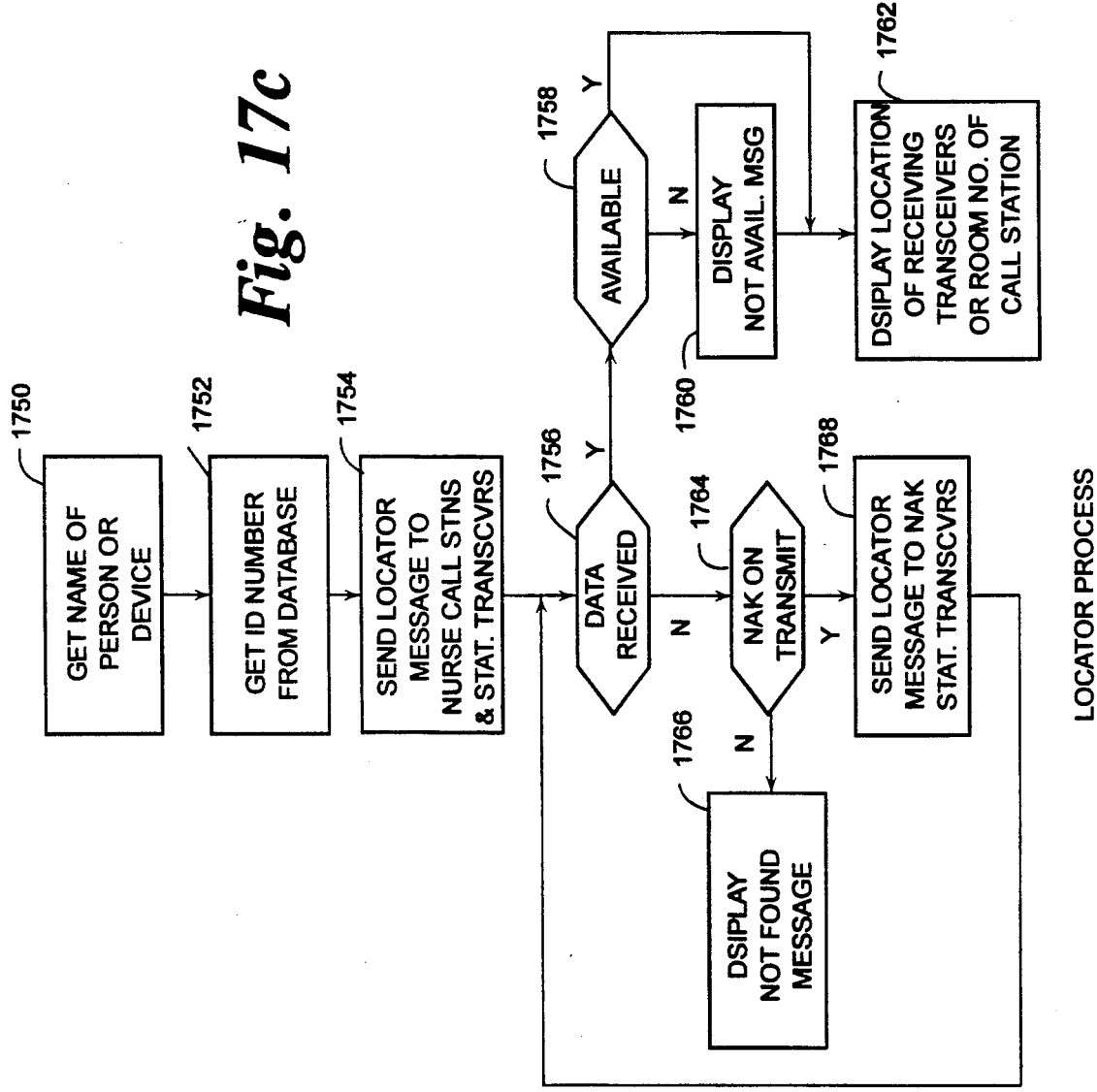

FIG. 17c illustrates how the memory cards 110 and 110' may be used in a locator system. At step 1750, an operator at the central computer 432 enters the name of the person or equipment which is to be located. The central computer 432 then accesses a database, at step 1752, to get the identification number associated with the name. Next, at step 1754, the central computer 432 broadcasts a locator message to all nurse call stations 210 and to all stationary transceivers.

At step 1756, the central computer determines if an ACK message was received having identifying information that matches that of the person or equipment that is to be located. If a match is found, step 1758 is executed to determine if the memory card is marked as available. If not, step 1760 is executed to display a not available message. This message is displayed simultaneously with the location message generated at step 1762.

If, at step 1758, the target ACK message was not received, step 1764 is executed to determine if there were any NAK responses to the message transmitted at step 1754. If there were, step 1768 is executed to retransmit the message to the call stations and fixed transceivers which responded with a NAK. Step 1768 transfers control to step 1756, described above. If, at step 1764, there were no NAK responses on the transmit, indicating that the message was received and processed properly by all call stations and transceivers to which it was broadcast, step 1766 is executed to display a message indicating that the individual or equipment was not found.

The process illustrated in FIG. 17d builds upon the locator process shown in FIG. 17c to produce a process that attempts to automatically assemble a team of specialists and equipment to respond to an emergency situation. In the first step in the process, step 1770, the central computer 432 determines the types of specialists and equipment that are needed. This information may be entered from a nurse station based on the condition of a patient. The condition maybe sent to the nurse station with a patient initiated nurse call request, as set forth above, it may be sent automatically when the call station senses an alarm condition, such as an irregular heart beat, from data provided by external equipment.

It is contemplated that the nurse station would display a menu of, for example, five types of emergency situation, each requiring a different mix of personnel and equipment. One of these situations would be indicated to the central computer 432. This indication would provide the central computer with the types of specialists and equipment needed and an indication of which nurse station initiated the call.

Alternatively, an emergency alert may be generated by a caregiver pressing the switch 1118 on her badge transceiver. In this instance, a set of specialists and equipment would be assembled that could handle any situation.

At 1772, the computer 432 searches its personnel and equipment database to obtain a list of identifiers for each specialty type and for each type of equipment.

At step 1774, the computer 432 uses the locator process shown in FIG. 17b to determine the location of each individual and piece of equipment on each list. A second database is then consulted to determine which of these individuals and equipment is available for use and is closest to the emergency.

Next, at step 1776, the computer 432 initiates a sequence of call messages to each of the selected individuals and a sequence of alarm messages to each of the selected pieces of equipment. The computer 432 also conditions the PBX 430 to ring the telephone set that is closest to the selected entities with a distinctive ring.

The call messages conditions the badge holder to emit a pulsed tone indicating that the individual is being called. In response to this message, the individual would know to find the nearest phone with the distinctive ring and either listen for the emergency message or see the message on the telephone's LCD display. When the individual has received the message, he may press the switch 1118 to indicate that he has responded. When this response is sensed, the computer 432 will stop sending call messages.

The alarm messages cause a badge holder attached to the piece of equipment to continually emit a relatively loud alarm tone. When the phone closest to the equipment is answered, the answerer is instructed to deliver the equipment to the nurse station. The alarm tone may be terminated by pressing a switch 1118 on the badge holder that is attached to the piece of equipment. This sends a response message to the central computer 432.

At step 1778, the central computer waits for a fixed amount of time, for example 30 seconds, to determine if all of the selected individuals and equipment have responded. If so, the responders are marked as unavailable and a full response message is displayed at the initiating nurse station 300 or at the nurse station closest to the individual who initiated the emergency alarm condition. This message includes a list of all of the equipment and personnel that have responded.

If, at step 1778, the central computer determines that some needed specialists or equipment have not responded, the lists from which the responders were drawn are deleted and the non responders are deleted from the remaining lists. These lists are then passed to step 1774, described above, to locate the next closest specialists and equipment.

The processes outlined above illustrate a few applications of a distributed processing system which may be coupled to multiple personal databases. All of these applications are in a hospital environment. A system of this type has significant medical and non-medical uses outside of a hospital environment.

Figure 18:
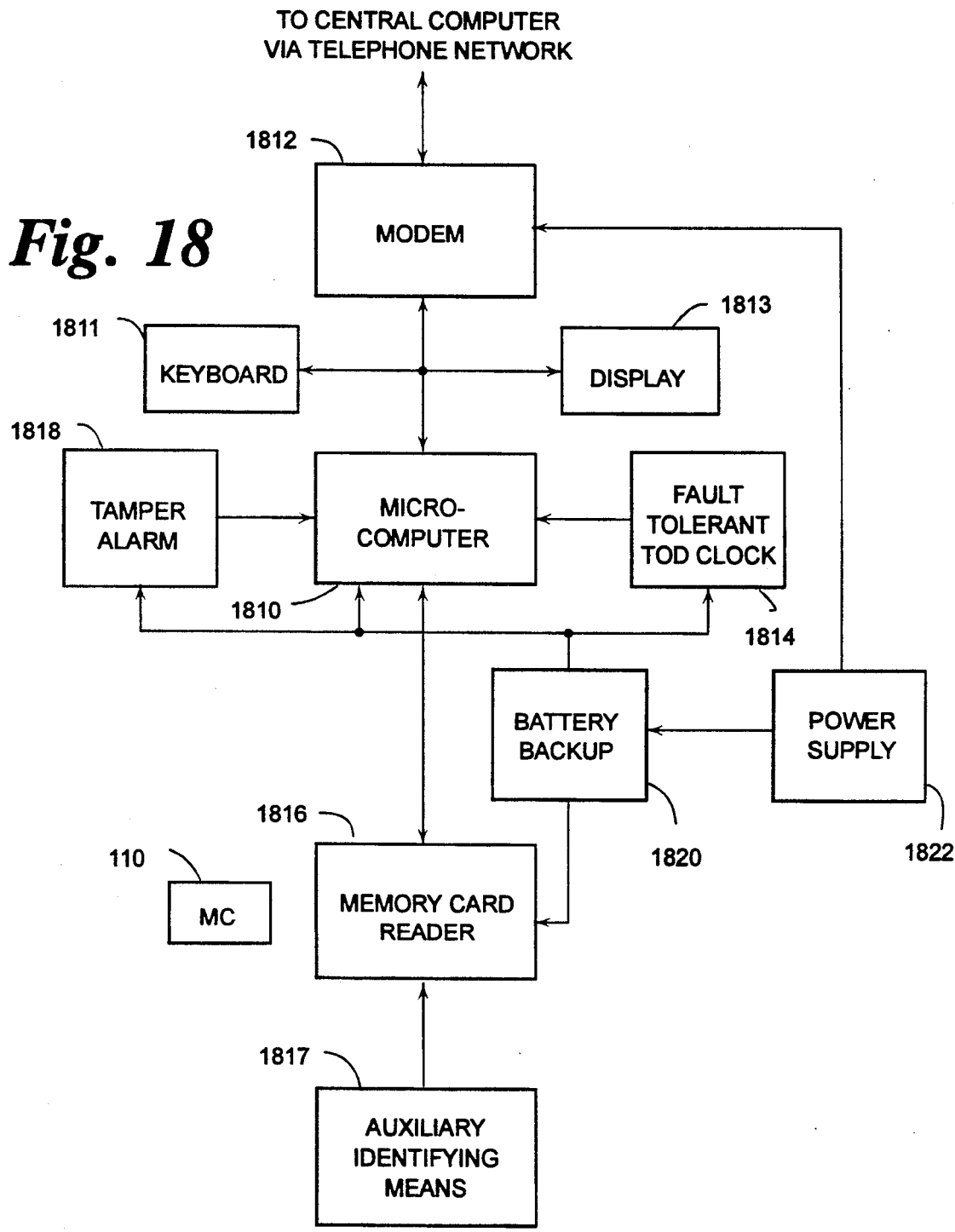
FIG. 18 is a block diagram of a secure doctor's services monitoring system which includes an embodiment of the present invention.

FIG. 18 is a block diagram of a secure billing system for physicians and other professionals whose charges are based on the amount of time spent with a patient or client. To simplify the description, it is assumed that the system is located in a physician's office and is used for billing Medicare for services provided by the physician.

In general terms, the system operates as follows. Each physician would be provided with one system. When the physician is attending to each patient, that patient's card is inserted into the system. The system records identifying information from the card and is provided, either by the doctor or by other office personnel with a diagnosis for the individual. At the end of the day, the system automatically dials up a central computer and transfer the day's billing information. This information is then processed to determine the amount due to the physician. This type of system would speed the processing of Medicare bills by eliminating much of the paper work. In addition, it is advantageous because it is more difficult to generate fraudulent bills using a system of this type.

As shown in FIG. 18, an exemplary system of this type includes a microcomputer 1810 which is coupled to a modem 1812 through which data may be communicated to the central database. In addition, the microcomputer 1810 is coupled to a keyboard 1811 and display device 1813 which may be used to enter data, such as a diagnosis or prescription information into the computer system. These components exist in many commercially available personal computer systems, for example, those that are compatible with the IBM Personal Computer.

In addition to these basic computer components, the system shown in FIG. 18 includes a fault tolerant time of day (TOD) clock 1814, a tamper alarm system 1818, a memory card reader 1816 and a power supply 1822 with a battery backup 1820. The system may also include auxiliary identifying means 1817, such as a commercially available fingerprint reader which can compare a person's fingerprint against data describing the fingerprint which is stored on the memory card 110.

The fault tolerant TOD clock 1814, tamper alarm system 1818 and battery backup 1820 ensure that the data provided by the billing system is accurate. The fault tolerant clock may be, for example, of the type describe-d in a paper by D. Davies et al. entitled "Synchronization and Matching in Redundant Systems", IEEE Trans. on Computers, June, 1978, pp 531–539, which is hereby incorporated by reference. The nature of the tamper alarm system would depend on the construction of the overall billing unit. At a minimum, the tamper alarm would detect: any attempt to open the case enclosing the unit and the insertion of an object other than a data card into the data card reader. Any detected tampering would condition the system to both sound an audible alarm and record the tampering event. Optionally, the tamper alarm system could also disable the device. Any recorded tampering events are sent to the central database with the billing information.

The power supply 1822 and battery backup 1820 provide power to the tamper alarm 1818, microcomputer 1810, fault tolerant clock 1814 and memory card reader 1816 even when no power is applied to the billing unit. The power supply and battery backup may be any of a number of commercially available components. The exact type of components used would depend on the power requirements of the system and on the types of interruption that may be expected.

Figure 19:
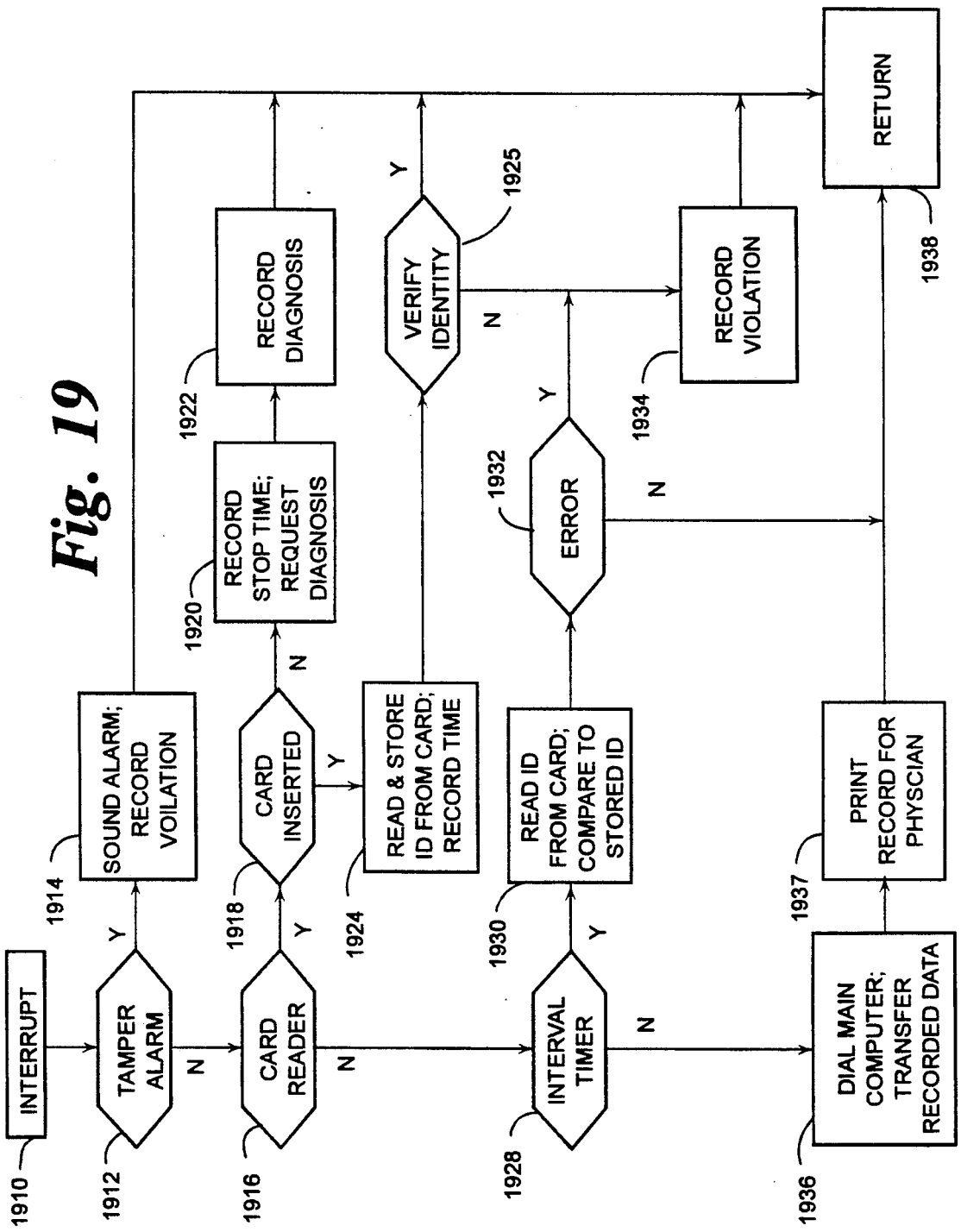
FIG. 19 is a flow-chart diagram which illustrates the operation of the monitoring system shown in FIG. 18.

FIG. 19 is a flow-chart diagram which illustrates the program that controls the billing system shown in FIG. 18. This program is desirably stored on ROM located securely within the case of the unit. The process shown in FIG. 19 operates in the background of other processing performed on the microcomputer 1810. Thus, the entire unit may be sold as a general purpose computer system for word processing or general billing. while the automatic billing function runs in a background mode.

In this configuration, care must be taken to ensure that no program which can interfere with the automatic billing operations is allowed to run on the system.

The first step in the program, step 1910, receives an interrupt. The interrupt may be from the tamper alarm 1818, memory card reader 1816, or fault-tolerant TOD clock 1814. If, at step 1912, the interrupt is from the tamper alarm, step 1914 is executed which sounds the audible alarm and records the tampering event. After recording the tampering event, the process, at step 1938, returns control to the program that was running when the interrupt occurred.

If, at step 1916, the interrupt is caused by the memory card reader 1816, step 1918 is executed to determine if the interrupt is caused by a card being inserted or by a card being removed. If a card has just been inserted, step 1924 is executed to read the identifying information from the card and store this information and the current time for later transmission to the central database. Optionally, after step 1924 has been executed, step 1925 may be invoked to verify the identity of the patient. In the exemplary embodiment, this identification is accomplished by comparing fingerprint information stored on the card with the actual fingerprint of the patient. If the identity is verified, control is transferred to step 1938, described above. Otherwise, control is transferred to the tamper alarm step 1914, described above.

If, at step 1918, the card reader interrupt is caused by a memory card being removed from the card reader 1816, step 1920 is executed to record the stop time and request a diagnosis for the patient. Either the physician or other office personnel enters the diagnosis which is recorded at step 1922. After step 1922, control is transferred to step 1938, described above.

In the exemplary embodiment of the invention, if the interrupt is not caused by the tamper alarm or the card reader, then it must be caused by the clock circuit 1814. At step 1928, the process determines if the clock interrupt is from the interval timer. If so, step 1930 is executed to read the identification information from the card and compare it to the stored identification for the individual. If any difference is detected, a violation is recorded at step 1934. After step 1934 or if no error is detected at step 1932, control is transferred to step 1938.

If the clock interrupt is not an interval timer interrupt then it is an indication that it is time to transfer the accumulated billing data to the main computer. In this instance, step 1936 is executed. -This step dials the main computer and transfers the recorded data along with data identifying the physician. In addition, the computer, at step 1937, may condition a printer (not shown) to print out a record of the data transferred for the physician's records. After step 1937, control is transferred to step 1938 to return control to the program running at the time the interrupt occurred.

The system described above in reference to FIGS. 1–16 may be used in a hospital environment to monitor the usage of controlled substances such as prescription drugs. FIGS. 20a through 20e illustrate an exemplary system for auditing drugs which are stored in a drug locker. The invention does not significantly impede the access of individuals to the drug locker, this would be done in using normal physical security measures such building locker from heavy gauge steel and placing a lock on the door.

Figure 20A:
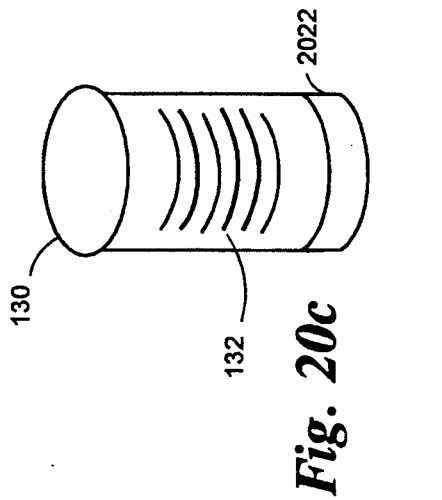
FIG. 20a is a cut away top plan view of a drug locker which includes an embodiment of the present invention.

FIG. 20a is a cut-away top plan view of a drug locker 2010 in accordance with this embodiment of the invention. As shown, the drug locker is a physically secure cabinet having a door 2011 that may be locked and containing several medicine containers 130. A stationary transceiver 2014 of the type described above with reference to FIG. 15 is positioned close to the drug locker. In addition, inside the locker a bar-code reader 2016 is positioned next to the door 2011 and a removal detector 2018 is concealed in the floor of the locker, positioned so that any containers removed from the locker must be passed over the detector 2018.

Figure 20C:
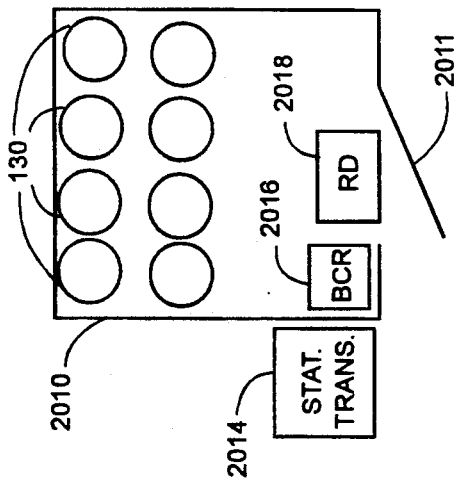
FIG. 20c is a perspective drawing of a medication container which may be used with the drug locker monitoring system shown in FIG. 20b.

The detector 2018 may be a resonance detector of the type commonly found in libraries and book stores which detects an induced resonant signal in a reactive component 2022 attached to the bottom of each medicine container 130, as shown in FIG. 20c.

Figure 20B:
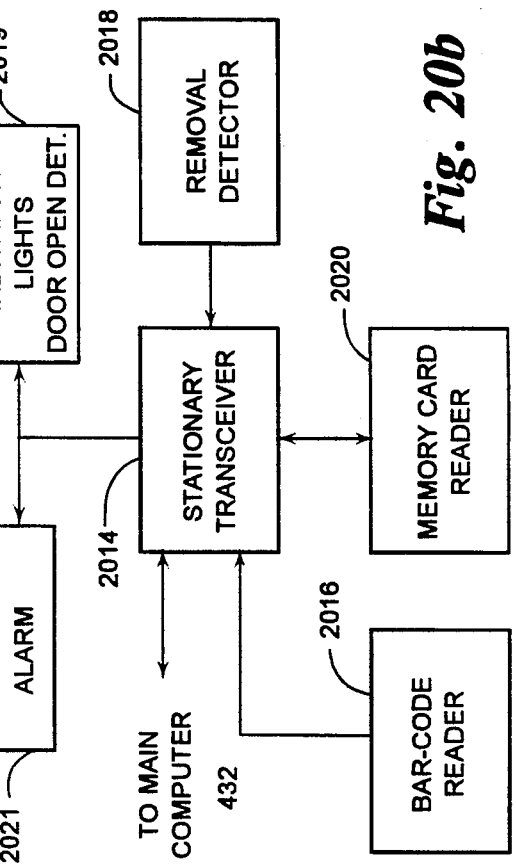

FIG. 20b is a functional block diagram of the drug monitoring system used in the drug locker. In addition to the components shown in FIG. 20a, the system shown in FIG. 20b includes an audible alarm 2021 a bar-code reader 2016, indicator lights and a door open detector 2019. All of the system elements 2016 through 021 are configured to be controlled by the microcontroller 1512 of the stationary transceiver, as shown in FIG. 15. The stationary transceiver is, in turn, controlled by the central computer 432.

FIG. 20d is a flow-chart diagram which illustrates the portion of the drug audit process that utilizes the circuitry shown in FIG. 20c. At step 2050, the opening of the door 2011 conditions the transceiver 2014, at step 2052, to transmit an authorization request to the badge transceiver worn by the individual opening the door. Since the identity of the individual is unknown, the identifier transmitted with the message is one that matches all assigned identifiers. In response to this request, the badge transceiver transmits authorization information, including the identity of the individual, to the stationary transceiver.

If, at step 2054, authorization information has not been received, the individual accessing the drugs may have inserted her card in the memory card reader 2020. At step 2056, the card reader is checked for authorization information. Step 2058 analyzes the received information to determine if the user is authorized to access the drug locker. If not, an alarm is sounded at step 2060 and the unauthorized access is recorded on the central computer 432.

If the individual is authorized to access the locker, step 2064 records the identifying information and the authorization information on the central computer 432. As each medicine container is removed from the locker, it is scanned by the bar-code reader. When the bar-code information has been scanned, the process changes a value in a memory location to indicate that the container may be removed.

At step 2070, the removal of a medicine container activates an interrupt in the microcontroller 1512. In response to this interrupt, the microcontroller, at step 2072 determines if the removal has been authorized. If not, step 2060 is executed to sound the alarm and record the unauthorized removal.

If, at step 2072, it is determined that the removal is authorized then, at step 2074, a light is turned on to indicate that the medicine may be removed and the type of medicine and time of removal is recorded both in the central computer 432 and on the memory card 110'.

Due to the relative positioning of the bar-code reader 2016 and the removal detector 2018, the indicator light will be lit while the medicine container is being scanned. An attempt to remove the container without scanning its bar-code will generate an audible alarm. The apparatus shown in FIGS. 20a through 20c may also be programmed to register and record when medicine containers are returned to the drug locker. In this process (not shown), the bar-code reader 2016 includes a second scanner (not shown) to scan the medicine containers before the door is opened. A sequence of events that would not sound an alarm would be: scan container using the outside scanner, detect door opening, simultaneously detect removal (actually a return) and scan using the inside scanner. Additionally, an electronic scale may be included in the floor of the drug locker to record the weight of the containers both as they are removed and returned. This information, when combined with the type of medicine would indicate the amount of medicine that has been distributed.

The circuitry and process shown in FIGS. 20a through 20c implements one-half of the drug auditing process. The other half is implemented at the nurse call station located near the patient's bed. As shown in FIG. 20e, the first step in this part of the process, step 2080, is to scan the patient's bar-code using the light pen 222, shown in FIG. 2. Next, at step 2082, the bar code 132 on the medicine container 130 is scanned. At step 2086 the call station microcomputer 414 searches the information on the patient's memory card for the scanned medicine. If the medicine is not found, an alarm is sounded at step 2088 to alert the caregiver that the medicine should not be administered. The alarm event, the identity of the medicine and the identity of the patient are also recorded on the central computer 432 at step 2088.

If, at step 2086, a match is found between the medicine and the information on the patient's memory card, step 2090 records the administration of the drug in the central computer 432 and on the patient's memory card 110.

The use of prescription medicines may be monitored from the information provided to the central computer 432. This information indicates the individuals who had access to the drug locker, the time they removed and returned the medicines, the patients to whom the medicines were administered, the prescribed doses and, optionally, the amount of medicine that was removed and the amount that was returned. This entire auditing process could take place without significantly impeding access to the drug locker.

All of the applications described above relate in some manner to the health care field. It is contemplated, however, that significant applications for the invention exist in areas other than health care. FIGS. 21a and 21b relate to an application of the invention which establishes a student information link in through a special telephone set in the student's dormitory room.

Figure 21B:
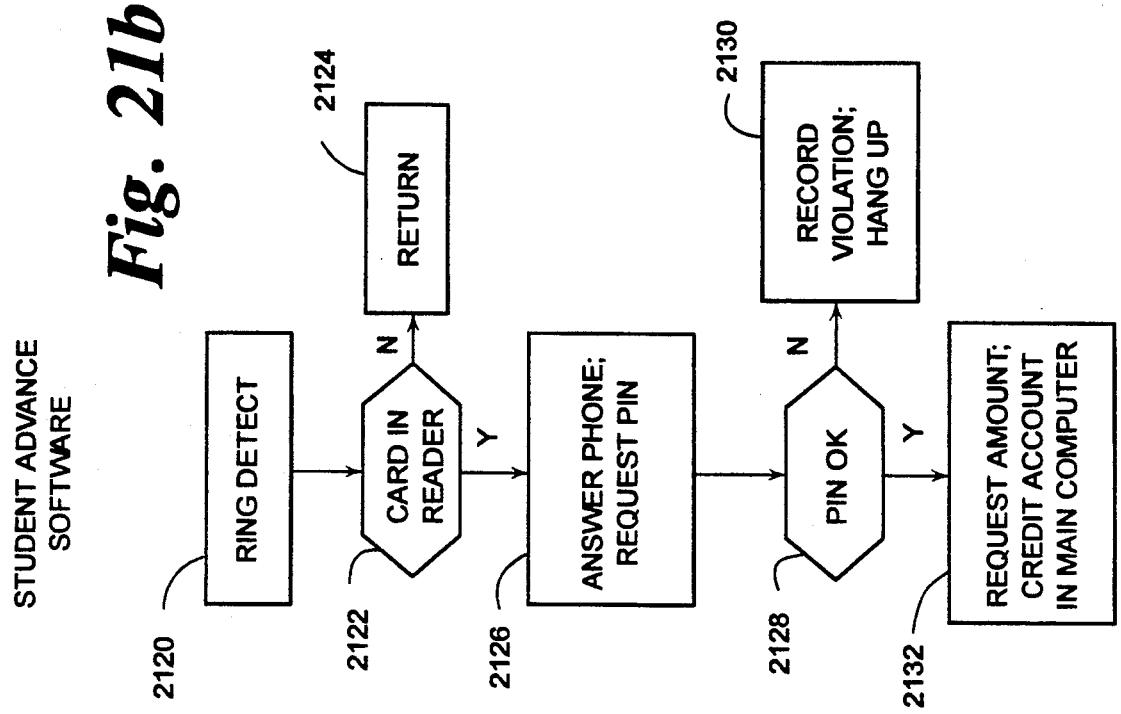
Figure 21A:
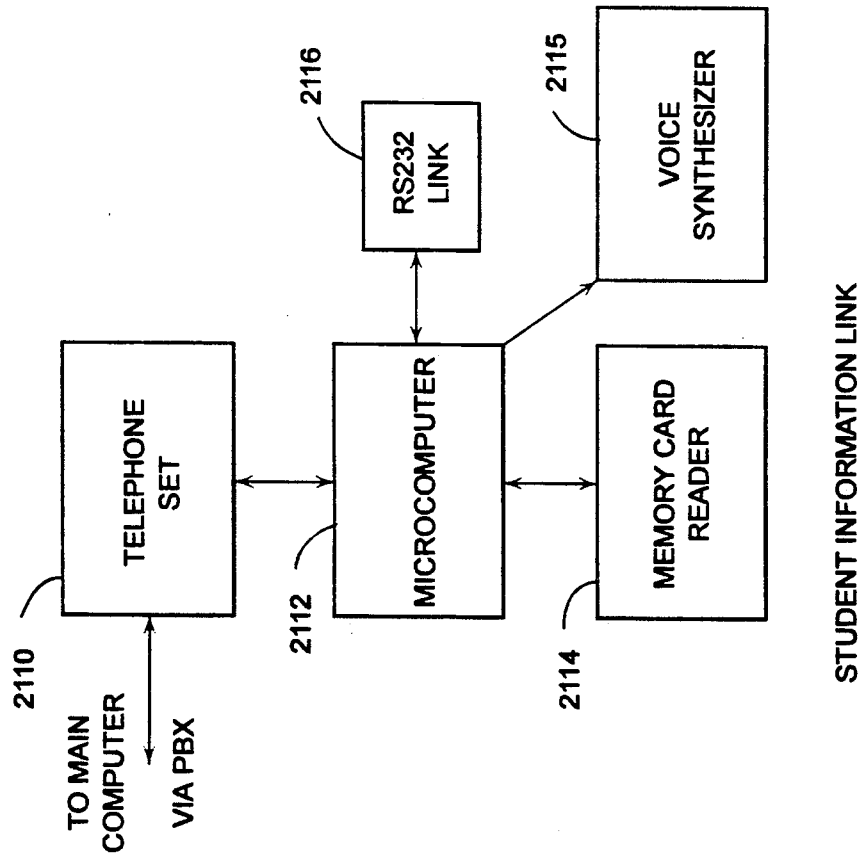
FIG. 21a is a block diagram of a student information system which includes an embodiment of the present invention.

As shown in FIG. 21a, the telephone set 2110 is coupled to a microcomputer, a memory card reader/writer 2114 and a digital data port, such as an RS232 link 2116. A data link between a central computer (not shown), the memory card reader/writer 2114 and the RS232 link 2116 is established through the telephone set 2110 which is coupled to a PBX (not shown). This network may be configured in the same manner as the network N2 shown in FIG. 14 above.

In this configuration, the memory card may be used as a standard identification card for directly billing telephone calls or to allow access to student records, assignment information, or a student bulletin board, via a personal computer coupled to the RS232 port.

In addition, the memory card may be used for a novel form of electronic funds transfer (EFT) as illustrated in FIG. 21b. Used in this manner, the student first calls home to request funds from his parents. He then hangs up and inserts his card in the phone. The parent calls back and, at step 2120, the ring is detected. At step 2122, the microcomputer 2112 determines if the card is in the reader. If not, step 2124 aborts the process and the phone call is handled normally.

If the card is in the reader 2114 at step 2122, step 2126 is executed and the microcomputer 2112 automatically answers the phone and requests the parent to enter her personal identification number (PIN). At step 2128, the microcomputer 2112 determines if the PIN is valid. If not, the connection is terminated and the violation is recorded at the main computer. If the PIN is valid, then at step 2132, the parent is prompted to key in the amount, the voice synthesizer 2115 is conditioned to repeat the amount and to request a verification. When the verification is received, the student's card is credited with the amount and an entry is made in the central computer to bill the parent for the amount.

In this embodiment of the invention, the credit on the card may be used only at specified locations on campus, for example, at the book store. As the funds are spent, a record is made of the purchases and this record is sent to the parent with the next account statement.

It is also contemplated that a locator and emergency alert system such as described above in reference to FIGS. 11 through 17 may be used in a corrections environment to determine the location of prison guards and trustees and to allow a prison guard to signal an emergency alert. This locator system may also be used as an automatic key station. For this use of the system, a network of the same type as the network N2 shown in FIG. 14 may be set up inside of a factory or office building. In this network, each of the stationary transceivers is programmed to continually transmit an identification request message. As a guard, wearing a badge transceiver passes the transceivers, the identity information is read from the card and stored in a central computer. This system has advantages over the traditional key station system since the guard need not carry the bulky clock device and since the location of the stationary transceivers may be concealed making it more difficult for the guard to defeat the system by taking a different route.

Furthermore, it is contemplated that the stationary transceivers and badge transceivers of the automated key station may be used, during normal business hours, as a phone forewarding system, similar to that implemented with the PLS-4000 Personnel Locating System manufactured by TELOC Inc. In this system, a user may instruct the PBX to forward his calls to his badge. Upon receiving the call, the PBX invokes a locator function, similar to that described above in reference to FIG. 17c. When a stationary transceiver relays a response message from the badge to be located, the PBX sends a beep message to the badge and routes the call to the telephone set coupled to the stationary transceiver that received the response.

While the invention has been described in terms of several exemplary embodiments, it is contemplated that it may be practiced with modifications within the spirit and scope of the appended claims.

The invention claimed is:

1. Apparatus for automating routine communication and location determination, comprising:
   portable database means for holding entity information including identification information about an entity;
   portable first communications means, removably coupled to said portable database means and said entity for retrieving the entity information including the identification information from said portable database means and for sending the retrieved information to a first remote location;
   second communications means, located at said first remote location, for receiving the retrieved information sent by said first communications means and for sending a message including at least a portion of said retrieved information to a second remote location; and
   central processor means, located at the second remote location, for receiving the message sent by said second communications means to maintain a central database and for determining the location of said entity.

2. The apparatus of claim 1 wherein:
   the entity information includes data relating to the amount of time that the database is coupled to the first communications means; and
   the second communications means includes means for calculating a fee based for the entity identified by the identifying information based on the time data provided by said first communications means.

3. The apparatus of claim 2, further including:
   means for detecting attempts to tamper with one of the database, the first communications means and the second communications means; and
   means for automatically transmitting data disclosing the detected tampering attempts to said second communications means.

4. The apparatus of claim 3 wherein the first communications means includes a first source of operational power and a second self contained source of operational power, the second source of operational power being coupled to apply power to at least a portion of the first communications means upon an interruption of power from the first source of operational power.

5. The apparatus of claim 1 wherein:
   said first communications means includes means for transmitting said entity information including said identification information using electromagnetic radiation; and
   said second communications means includes means for receiving said entity information transmitted by said first communications means.

6. The apparatus of claim 5 wherein:
   said second communications means includes means for broadcasting data to said first communications means using electromagnetic radiation; and
   said first communications means includes;
   means for receiving the data broadcast by the second communications means; and means for storing at least a portion of the data received from the second communications means into said portable database means.

7. The apparatus of claim 6 wherein the information transmitted by said first communication means is transmitted using a predetermined signal strength for the electromagnetic radiation and first communications means includes means for momentarily increasing the signal strength used to transmit said entity information.

8. The apparatus of claim 7 further including:
a plurality of second communications means distributed over an area;
wherein said central processor means includes a display device, coupled to said plurality of second communications means, (1) for causing each of said second communications means to send a message to said first communications means and to await for a response therefrom, (2) for identifying, based on the received responses, one of said second communications means as being physically close to said first communications means, (3) for displaying the position of said identified
means for storing at least a portion of the data received from the second communications means into said portable database means.

9. The apparatus of claim 6 further including:
a plurality of said second communications means;
a telephone network including a plurality of telephone sets coupled to respectively different ones of said plurality of second communications means; and
means, coupled to said telephone network for identifying which of the second communications means is physically close to the first communications means and for establishing a connection from a predetermined node in the telephone network to the telephone set coupled to the identified second communications means.

10. Apparatus for automating routine communication comprising:
portable database means for storing entity information including identification information about an entity;
first communications means, removably coupled to said portable database means for retrieving the entity information including the identification information from said portable database means and for sending the retrieved information to a first remote location;
second communications means, located at said first remote location, for receiving the retrieved information sent by said first communications means and for sending a message including at least a portion of said retrieved information to a second remote location; and
central processor means, located at the second remote location, for receiving the message sent by said second communications means to maintain a central database; wherein
the portable database means is a memory card;
the entity information includes medical information pertaining to a patient in a hospital;
the first communications means includes a nurse call station having means for requesting assistance from a nurse; and
the second communications means includes a central nurse station having means for displaying the identification information and medical information sent from the database in response to the request for assistance from said first communication means.

11. The apparatus of claim 10, further including:
identification means, configured to be non-removably affixed to the patient, for holding machine-readable identification information relating to the patient;
reading means, coupled to said nurse call station for reading said machine-readable identification information; and
means, coupled to said nurse call station, for comparing the machine-readable identification information to the identification information held by said memory card.

12. The apparatus of claim 11 wherein:
said medical information includes data identifying prescribed medications;
said reading means includes means for reading machine-readable data identifying one of the prescribed medications from a container which holds the one prescribed medication; and
said first communications means includes:
means for searching the information held in the memory card for data identifying the prescribed medications which matches the data provided by said reading means from said container of prescribed medication; and
means for indicating an alarm condition when no match is found between the data held by the memory card and the data provided by said reading means from the container of prescribed medication.

13. The apparatus of claim 12 wherein:
the data identifying prescribed medications includes data specifying a time at which the medication is to be administered;
the first communications means includes:
clock means for developing digital signals representing the current time;
comparison means for comparing the digital samples provided by the clock means with the medication time data held by said memory card; and
means for causing said first communications means to send the identification information and the data identifying one of the prescribed medications to said second communications means when said comparison means finds a match between the signals provided by the clock means and the medication time data for said one prescribed medication.

14. The apparatus of claim 13 wherein said first communications means includes means for storing, onto said memory card, information relating to the time that the data is read from the medication container, when a match is found by said searching means, the stored time information being associated with the data identifying said one prescribed medication.

15. The apparatus of claim 12 wherein:
the machine-readable identification information non-removably affixed to the patient includes bar-coded data;
the machine-readable information on the medicine container includes bar-coded data; and
the reading means includes a light pen, coupled to said first communications means.

16. Apparatus for automating routine communication and location determination comprising:

a plurality of portable databases for holding entity information including identification information about a respective plurality of entities;

a plurality of portable communicators, each being removably coupled to a respective one of said entities and to a respective one of said plurality of portable databases for retrieving the entity information including the identification information and for sending the retrieved information to a remote location;

a plurality of receivers, each located at respective remote locations for receiving the entity information sent by one of said plurality of portable communicators and for sending a message including at least a portion of said received information to a second remote location; and a central processor, located at said second remote location, for receiving said message sent by one of said plurality of receivers to maintain a central database and to determine the location of said respective one of said entities.

17. The apparatus of claim 16 wherein:

the portable database is a memory card;

the entity information includes medical information pertaining to a patient in a hospital;

each of said portable communicators being coupled to a nurse call station having means for requesting assistance from a nurse and means for determining when medication is due to be administered to the patient based on information stored on the memory card; and each of said receivers includes a central nurse station having means for displaying the identification information and medical information automatically sent from one of the portable databases in response to one of (1) a request for assistance initiated at one of said portable communicators and (2) a determination that medication is due made by one of said portable communicators.

18. The apparatus of claim 17 wherein:

said plurality of receivers are interconnected such that communication among said plurality of receivers is maintained if said central processor fails.

* * * * *